(12) United States Patent
Harmelin et al.

(10) Patent No.: US 11,395,590 B2
(45) Date of Patent: Jul. 26, 2022

(54) MULTIMODAL TRANSCRANIAL BRAIN OPTICAL IMAGING

(71) Applicants: Yeda Research and Development Co. Ltd., Rehovot (IL); Ministry of Health on behalf of The Jerusalem Mental Health Center, Jerusalem (IL)

(72) Inventors: Alon Harmelin, Rishpon (IL); David Israeli, Rehovot (IL); Yuri Kuznetsov, Rehovot (IL); Vyacheslav Kalchenko, Rehovot (IL)

(73) Assignees: Yeda Research and Development Co. Ltd., Rehovot (IL); Ministry of Health on behalf of The Jerusalem Mental Health Center, Jerusalen (IL)

(*) Notice: Subject to any disclaimer, the term of this patent is extended or adjusted under 35 U.S.C. 154(b) by 1189 days.

(21) Appl. No.: 15/308,123

(22) PCT Filed: Apr. 30, 2015

(86) PCT No.: PCT/IL2015/050457
§ 371 (c)(1),
(2) Date: Nov. 1, 2016

(87) PCT Pub. No.: WO2015/166503
PCT Pub. Date: Nov. 5, 2015

(65) Prior Publication Data
US 2017/0100037 A1    Apr. 13, 2017

Related U.S. Application Data

(60) Provisional application No. 61/986,955, filed on May 1, 2014.

(51) Int. Cl.
*A61B 5/00* (2006.01)
*A61B 5/02* (2006.01)
(Continued)

(52) U.S. Cl.
CPC .......... *A61B 5/0035* (2013.01); *A61B 5/0042* (2013.01); *A61B 5/0071* (2013.01);
(Continued)

(58) Field of Classification Search
None
See application file for complete search history.

(56) References Cited

U.S. PATENT DOCUMENTS 7,620,265 B1    11/2009    Wolff et al.
2007/0249913 A1    10/2007    Freeman et al.
(Continued)

FOREIGN PATENT DOCUMENTS

WO    WO 2014/009859    1/2014
WO    WO 2015/166503    11/2015

OTHER PUBLICATIONS

Hillman et al. ("all optical anatomical co-registration for molecular imaging of small animals using dynamic contrast", Nat. Phot. 1(9): 526-530 (Year: 2007).*
(Continued)

*Primary Examiner* — Amelie R Davis
*Assistant Examiner* — Marjan Saboktakin

(57) ABSTRACT

A method of transcranial brain optical imaging including obtaining a Laser Speckle (LS) image of cranial blood vessels of a subject, obtaining a Dynamic Fluorescence (DF) image of the cranial blood vessels of the subject, and combining the LS image and the DF image producing a combined color image which displays both structure of the cranial blood vessels and perfusion of blood along the cranial blood vessels. Related apparatus and methods are also described.

21 Claims, 18 Drawing Sheets
(14 of 18 Drawing Sheet(s) Filed in Color)

(51) Int. Cl.
*A61B 5/026* (2006.01)
*A61B 5/024* (2006.01)
*G01N 21/47* (2006.01)
*G01N 21/64* (2006.01)

(52) U.S. Cl.
CPC ............ *A61B 5/0082* (2013.01); *A61B 5/024* (2013.01); *A61B 5/02007* (2013.01); *A61B 5/0261* (2013.01); *G01N 21/4795* (2013.01); *G01N 21/6456* (2013.01); *A61B 5/4064* (2013.01); *A61B 2576/026* (2013.01); *G01N 2201/068* (2013.01); *G01N 2201/06113* (2013.01)

(56) References Cited

U.S. PATENT DOCUMENTS

2009/0118622 A1   5/2009   Durkin et al.
2011/0301441 A1   12/2011  Bandic et al.
2013/0016886 A1   1/2013   Schoenmeyer et al.

OTHER PUBLICATIONS

Kalchenko et al. ("multimodal diagnostic approach for functional imaging of tumor vascular network and blood microcirculation", SPIE, (Year: 2011).*
Supplementary European Search Report and the European Search Opinion dated Apr. 11, 2018 From the European Patent Office Re. Application No. 15786002.4. (13 Pages).
Kur et al. "Cellular and Physiological Mechanisms Underlying Blood Flow Regulation in the Retina and Choroid in Helath and Disease", Progress in Retinal and Eye Research, XP028425605, 31(5): 377-406, Available Online May 3, 2012.
Schmetterer et al. "How Can Blood Flow Be Measured?", Survey of Ophthalmology, XP022338691, 52(6/Suppl.2): S134-S138, Nov. 2007. Abstract, p. S134, col. 1, Para 2—p. S135, col. 1, Para 2, p. S136, col. 1, Para 3.
International Preliminary Report on Patentability dated Nov. 10, 2016 From the International Bureau of WIPO Re. Application No. PCT/IL2015/050457. (10 Pages).
International Search Report and the Written Opinion dated Oct. 8, 2015 From the International Searching Authority Re. Application No. PCT/IL2015/050457.
Abramoff et al. "MRI Dynamic Color Mapping: A New Quantitative Technique for Imaging Soft Tissue Motion in the Orbit", Investigative Ophthalmology & Visual Science, 41(11): 3256-3260, Oct. 2000.
Baum et al. "Fusion Viewer: A New Tool for Fusion and Visualization of Multimodal Medical Data Sets", Journal of Digital Imaging, 21(Suppl.1): S59-S68, Online Publication Oct. 25, 2007.
Benndorf "Color-Coded Digital Subtraction Angiography: The End of A Monochromatic Era?", AJNR American Journal of Neuroradiology, 31(5): 925-927, May 2010.
Boas et al. "Laser Speckle Contrast Imaging in Biomedical Optics", Journal of Biomedical Optics, 15(1): 011109-1-011109-12, Jan./Feb. 2010.
Burton et al. "Multispectral Opto-Acoustic Tomography (MSOT) of the Brain and Glioblastoma Characterization", NeuroImage, 65: 522-528, 2013.
Chen et al. "Study on Reflection of Human Skin With Liquid Paraffin as the Penetration Enhancer by Spectroscopy", Journal of Biomedical Optics, 18(10): 105001-1-105001-5, Published Online Oct. 3, 2013.
Doronin et al. "Imaging of Subcutaneous Microcirculation Vascular Network by Double Correlation Optical Coherence Tomography", Laser & Photonics Reviews, 7(5): 797-800, 2013.
Dunn et al. "Dynamic Imaging of Cerebral Blood Flow Using Laser Speckle", Journal of Cerebral Blood Flow and Metabolism, 21: 195-201, 2001.

Engel et al. "Modeling Stroke in Mice—Middle Cerebral Artery Occlusion With the Filament Model", Journal of Visualized Experiments, 47: e2423-1-e2423-5, Jan. 2011.
Feng et al. "A Fusion Algorithm for GFP Image and Phase Contrast Image of *Arabidopsis* Cell Based on SFL-Contourlet Transform", Computational and Mathematical Methods in Medicine, 2013(ID635040): 1-10, 2013.
Glover et al. "Malarial Retinopathy and Fluorescein Angiography Findings in a Malawian Child With Cerebral Malaria", The Lancet Infectious Diseases, 10(6): 440, Jun. 2010.
Goelitz et al. "Parametric Color Coding of Digital Subtraction Angiography in the Evaluation of Carotid Cavernous Fistulas", Clinical Neuroradiology, 23(2): 113-120, 2013.
Habermehl et al. "Contrast Enhanced High-Resolution Diffuse Optical Tomography of the Human Brain Using ICG", Optics Express, 19(19): 18636-18644, Sep. 8, 2011.
Harb et al. "In Vivo Imaging of Cerebral Microvascular Plasticity From Birth to Death", Journal of Cerebral Blood Flow & Metabolism, 33: 146-156, 2013.
Hillman et al. "All-Optical Anatomical Co-Registration for Molecular Imaging of Small Animals Using Dynamic Constrast", Nature Photonics, 1(9): 526-530, 2007.
Hillman et al. "In Vivo Optical Imaging and Dynamic Contrast Methods for Biomedical Research", Philosophical Transactions of the Royal Society A, 369: 4620-4643, 2011.
Hong et al. "Through-Skull Fluorescence Imaging of the Brain in a New Near-Infrared Window", Nature Photonics, 8: 723-730, Published Online Aug. 3, 2014.
Kalchenko et al. "A Simple Approach for Non-Invasive Transcranial Optical Vascular Imaging (nTOVI)", Journal of Biophotonics, p. 1-5, First Published Online Apr. 29, 2015.
Kalchenko et al. "Combined Application of Dynamic Light Scattering Imaging and Fluorescence Intravital Microscopy in Vascular Biology", Laser Physics Letters, 7(8): 603-606, Published Online Jun. 1, 2010.
Kalchenko et al. "In Vivo Characterization of Tumor and Tumor Vascular Network Using Multi-Modal Imaging Approach", Journal of Biophotonics, 4(9): 645-649, 2011.
Kalchenko et al. "In Vivo Dynamic Light Scattering Microscopy of Tumour Blood Vessels", Journal of Microscopy, 228(Pt.2): 118-122, 2007.
Kalchenko et al. "Transcranial Optical Vascular Imaging (TOVI) of Cortical Hemodynamics in Mouse Brain", Scientific Reports, 4(5839): 1-7, Jul. 25, 2014.
Kamp et al. "Microscope-Integrated Quantitative Analysis of Intraoperative Indocyanine Green Fluorescence Angiography for Blood Flow Assessment: First Experience in 30 Patients", Operative Neurosurgery, 70(ON Suppl. 1): ons65-ons74, Mar. 2012.
Kang et al. "Quantitative Analysis of Peripheral Tissue Perfusion Using Spatiotemporal Molecular Dynamics", PLoS ONE, 4(1): e4275-1-e4275-11, Jan. 26, 2009.
Kneipp et al. "functional Real-Time Optoacoustic Imaging of Middle Cerebral Artery Occlusion in Mice", PLoS ONE, 9(4): e96118-1-e96118-6, Apr. 28, 2014.
Kohl-Bareis et al. "Noninvasive Monitoring of Cerebral Blood Flow by a Dye Bolus Method: Separation of Brain From Skin to Skull Signals", Journal of Biomedical Optics, 7(3): 464-470, Jul. 2002.
Koutsias et al. "The Use of Intensity-Hue-Saturation Transformation of Landsat-5 Thematic Mapper Data for Burned Land Mapping", Photogrammetric Engineering & Remote Sensing, 66(7): 829-839, Jul. 2000.
Ku et al. "Noninvasive Optical Measurement of Cerebral Blood Flow in Mice Using Molecular Dynamics Analysis of Indocyanine Green", PLoS ONE, 7(10): e48383-1-e48383-10, Oct. 31, 2012.
Li et al. "Imaging Cerebral Blood Flow Through the Intact Rat Skull With Temporal Laser Speckle Imaging", Optics Letters, 31(12): 1824-1826, Jun. 15, 2006.
Macrae "Preclinical Stroke Research—Advantages and Disadvantages of the Most Common Rodent Models of Focal Ischaemia", British Journal of Pharmacology, 164(4): 1062-1078, Oct. 2011.

(56) References Cited

OTHER PUBLICATIONS

Ntziachristos "Going Deeper Than Microscopy: The Optical Imaging Frontier in Biology", Nature Methods, 7(8): 603-614, Published Online Jul. 30, 2010.
Richards et al. "Low-Cost Laser Speckle Contrast Imaging of Blood Flow Using a Webcam", Biomedical Optics Express, 4(10): 1-15, Oct. 1, 2013.
Rink et al. "Minimally Invasive Neuroradiologic Model of Preclinical Transient Middle Cerebral artery Occlusion in Canines", Proc. Natl. Acad. Sci. USA, PNAS, 105(37): 14100-14105, Sep. 16, 2008.
Schindelin et al. "Fiji—An Open Source Platform for Biological Image Analysis", Nature Methods, 9(7): 676-682, 2012.
Schluter "Color Transform From RGB to IHS and Back", Image JIHS Color Transforms Plug-In, Apr. 31, 2014.
Stein et al. "Noninvasive, In Vivo Imaging of the Mouse Brain Using Photoacoustic Microscopy", Journal of Applied Physics, 105: 102027-1-102027-5, 2009.
Strother et al. "Parametric Color Coding of Digital Subtraction Angiography", AJNR American Journal of Neuroradiology, 31: 919-924, May 2010.
Towle et al. "Comparison of Indocyanine Green Angiography and Laser Speckle Contrast Imaging for the Assessment of Vasculature Perfusion", Neurosurgery, 71(5): 1023-1031, Nov. 2012.
Vakoc et al. "Three-Dimensional Microscopy of the Tumor Microenvironment In Vivo Using Optical Frequency Domain Imaging", Nature Medicine, 15(10): 1219-1223, Oct. 2009.
Winship "Laser Speckle Contrast Imaging to Measure Changes in Cerebral Blood Flow", Methods in Molecular Biology, Cerebral Angiogenesis: Methods and Protocols, 1135(Chap.19): 223-235, 2014.
Woitzik et al. "Cortical Perfusion Measurement by Indocyanine-Green Videoangiography in Patients Undergoing Hemicraniectomy for Malignant Stroke", Stroke, 37: 1549-1551, Apr. 27, 2006.
Zakharov et al. "Dynamic Laser Speckle Imaging of Cerebral Blood Flow", Optics Express, 17(16): 13904-13917, Jul. 27, 2009.
Zhang et al. "Functional Photaccoustic Microscopy for High-Resolution and Non-Invasive In Vivo Imaging", Nature Biotechnology, 24(7): 848-851, Published Online Jun. 25, 2006.
Zhou et al. "Dynamic Near-Infrared Optical Imaging of 2-Deoxyglucose Uptake by Intracranial Glioma of Athymic Mice", PLoS ONE, 4(11): e8051-1-e8051-9, Nov. 2009.
Communication Pursuant to Rule 164(1) EPC [Supplementary Partial European Search Report and the European Provisional Opinion] dated Jan. 3, 2018 From the European Patent Office Re. Application No. 15786002.4. (14 Pages).
Dunn "Laser Speckle Contrast Imaging of Cerebral Blood Flow", Annals of Biomedical Engineering, XP035016160, 40(2): 367-377, Published Online Nov. 23, 2011.
Sun et al. "Simultaneous Monitoring of Intracellular pH Changes and Hemodynamic Response During Cortical Spreading Depression by Fluorescence-Corrected Multimodal Optical Imaging", NeuroImage, XP028263794, 57(3): 873-884, Available Online May 23, 2011.
Communication Pursuant to Article 94(3) EPC dated Oct. 18, 2021 From the European Patent Office Re. Application No. 15786002.4. (4 Pages).

* cited by examiner

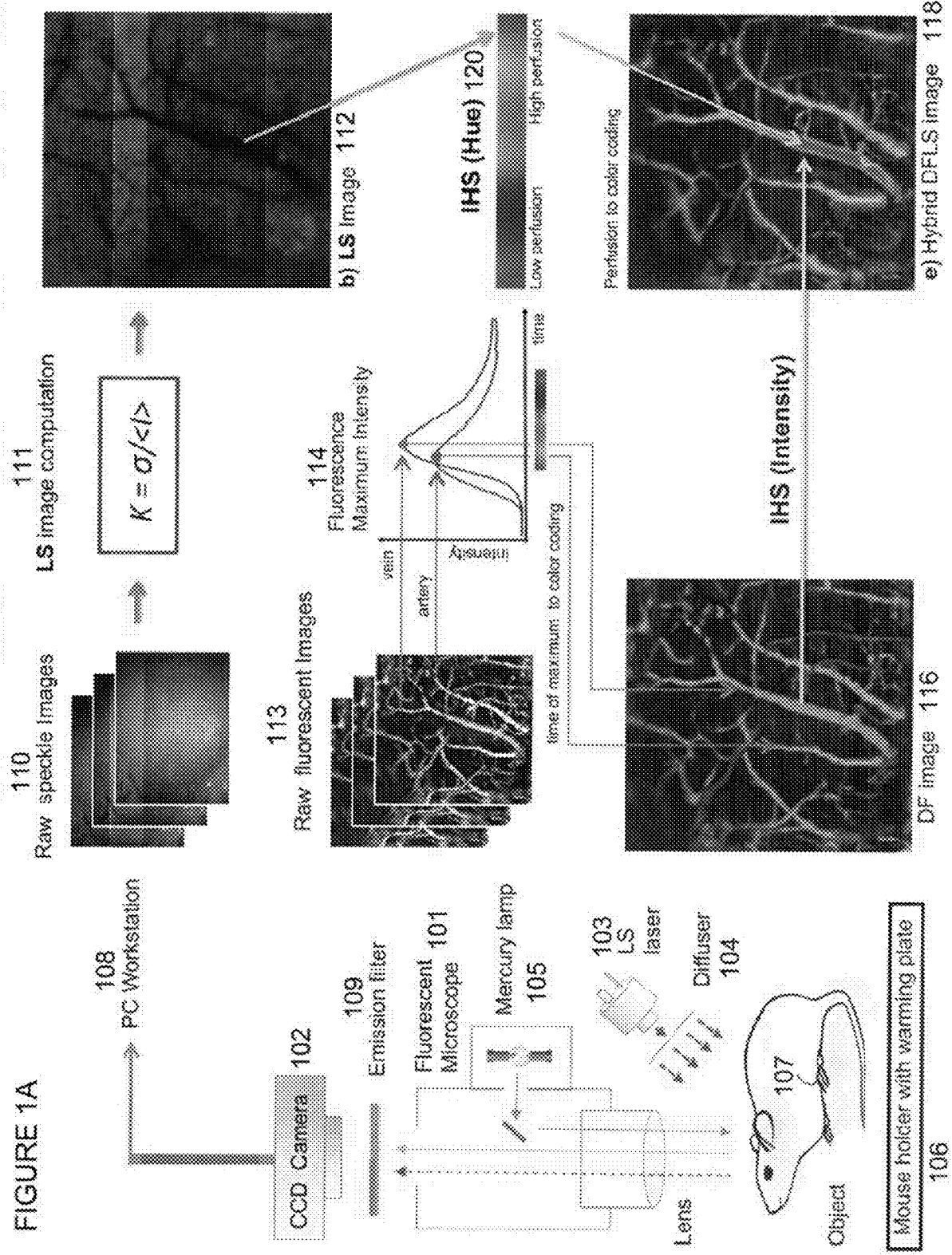

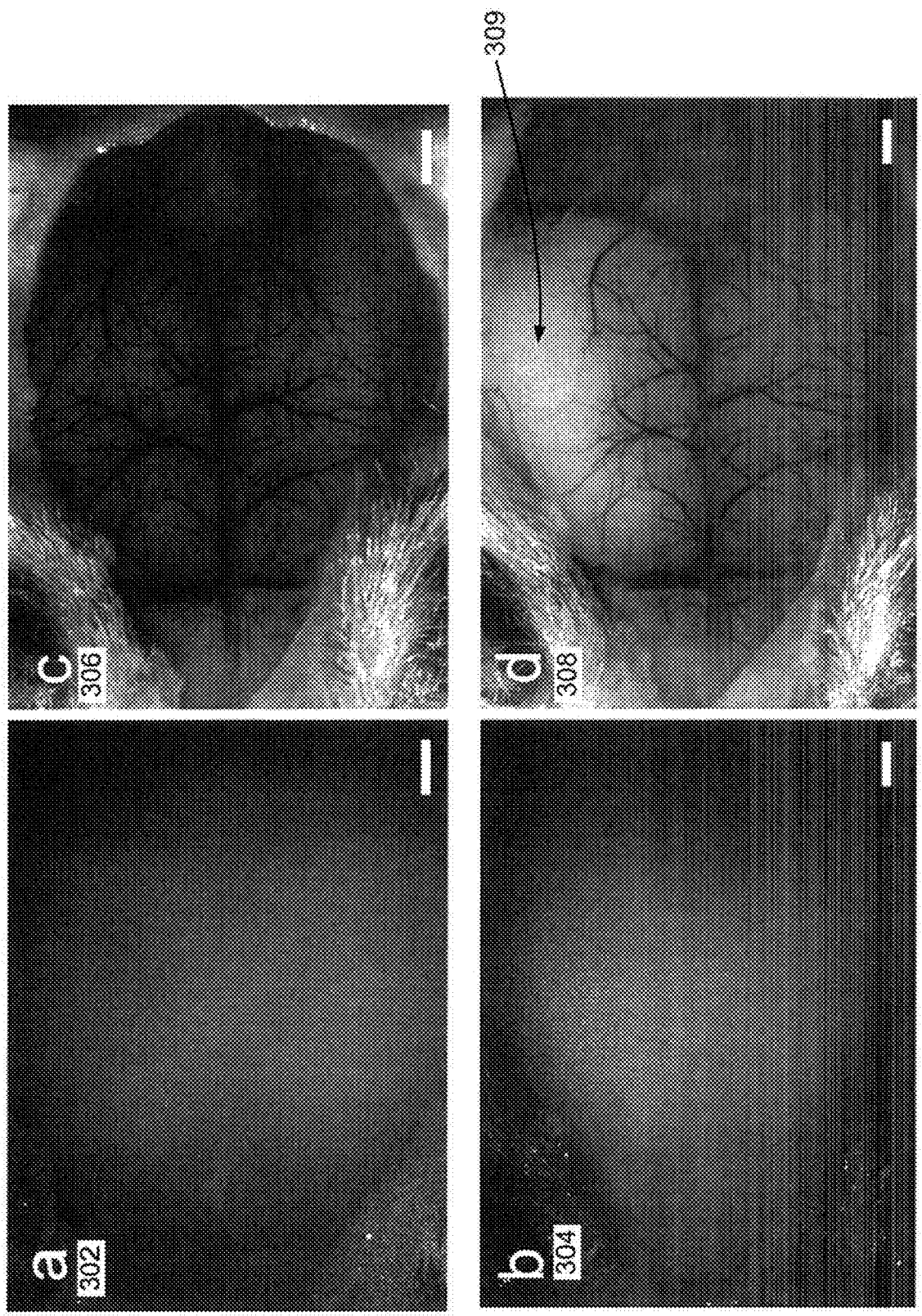

FIGURE 5B
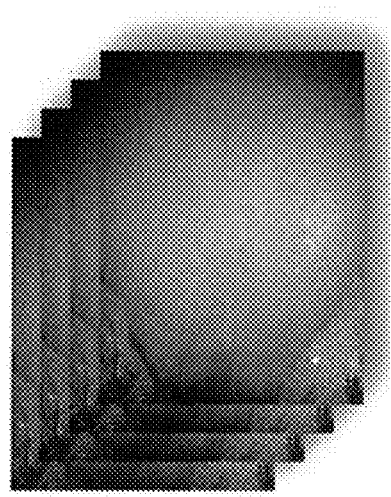
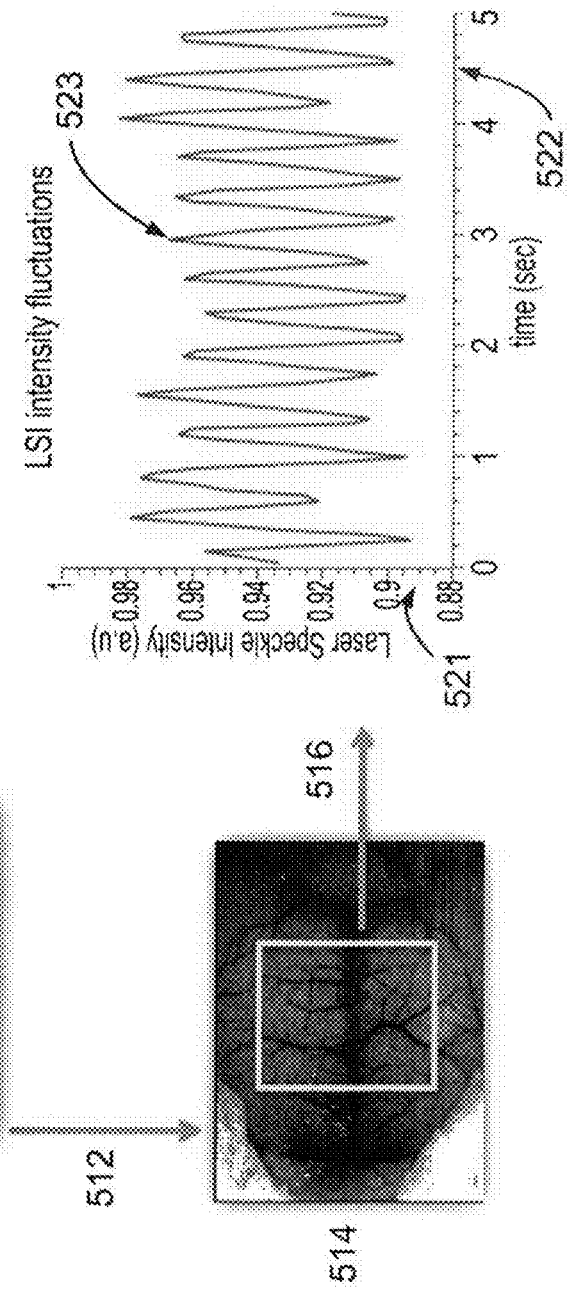

MULTIMODAL TRANSCRANIAL BRAIN OPTICAL IMAGING

RELATED APPLICATIONS

This application is a National Phase of PCT Patent Application No. PCT/IL2015/050457 having International filing date of Apr. 30, 2015, which claims the benefit of priority under 35 USC § 119(e) of U.S. Provisional Patent Application No. 61/986,955 filed on May 1, 2014. The contents of the above applications are all incorporated by reference as if fully set forth herein in their entirety.

FIELD AND BACKGROUND OF THE INVENTION

The present invention, in some embodiments thereof, relates to systems and methods for transcranial brain imaging and, more particularly, but not exclusively, to systems and methods for Transcranial Optical Vascular Imaging (TOVI) of cortical hemodynamics in mouse brain, and, even more particularly, but not exclusively, to displaying the imaging results.

In vivo imaging of the cortical blood vessels is essential for assessment of brain function under varying conditions in clinical and experimental settings.

Limitations such as removing or thinning at least part of a skull, and/or a need for use of expensive equipment such as CT and/or MRI, in order to perform in vivo imaging of the cortical blood vessels restrict the use of this procedure in settings such as preclinical trials.

Additional background art includes:

An article by Vakoc, B. J. et al., titled: "Three-dimensional microscopy of the tumor microenvironment in vivo using optical frequency domain imaging", published in Nat. Med. 15, 1219-1223 DOI: 10.1038/nm.1971 (2009).

An article by Stein, E. W., Maslov, K. and Wang, L. V., titled: "Noninvasive, in vivo imaging of the mouse brain using photoacoustic microscopy", published in J. Appl. Phys. 105, 102027 DOI: 10.1063/1.3116134 (2009).

An article by Burton, N. C. et al., titled: "Multispectral opto-acoustic tomography (MSOT) of the brain and glioblastoma characterization", published in NeuroImage 65, 522-528 DOI: 10.1016/j.neuroimage 0.2012.09.053. (2013).

An article by Harb, R., Whiteus, C., Freitas, C. and Grutzendler, J., titled: "In vivo imaging of cerebral microvascular plasticity from birth to death", published in J. Cereb. Blood Flow Metab. Off. J. Int. Soc. Cereb. Blood Flow Metab. 33, 146-156 DOI: 10.1038/jcbfm.2012.152 (2013).

An article by Towle, E. L., Richards, L. M., Kazmi, S. M. S., Fox, D. J. and Dunn, A. K., titled: "Comparison of indocyanine green angiography and laser speckle contrast imaging for the assessment of vasculature perfusion", published in Neurosurgery 71, 1023-1030; discussion 1030-1031 DOI: 10.1227/NEU.0b013e31826adf88. (2012).

An article by Kalchenko, V., Madar-Balakirski, N., Meglinski, I. and Harmelin, A., titled: "In vivo characterization of tumor and tumor vascular network using multi-modal imaging approach", published in J. Biophotonics 4, 645-649 DOI 10.1002/jbio.201100033. (2011).

An article by Boas, D. A. and Dunn, A. K., titled: "Laser speckle contrast imaging in biomedical optics", published in J. Biomed. Opt. 15, 011109 DOI: 10.1117/1.3285504 (2010).

An article by Kalchenko, V. et al., titled: "In vivo dynamic light scattering microscopy of tumour blood vessels", published in J. Microsc. 228, 118-122 DOI: 10.1111/j.1365-2818.2007.01832.x (2007).

An article by Dunn, A. K., Bolay, H., Moskowitz, M. A. and Boas, D. A., titled: "Dynamic imaging of cerebral blood flow using laser speckle", published in J. Cereb. Blood Flow Metab. Off. J. Int. Soc. Cereb. Blood Flow Metab. 21, 195-201 DOI: 10.1097/00004647-200103000-00002 (2001).

An article by Glover, S. J., Maude, R. J., Taylor, T. E., Molyneux, M. E. and Beare, N. A. V., titled: "Malarial retinopathy and fluorescein angiography findings in a Malawian child with cerebral malaria", published in Lancet Infect. Dis. 10, 440 DOI: 10.1016/51473-3099(10)70073-6 (2010).

An article by Kamp, M. A. et al., titled: "Microscope-integrated quantitative analysis of intraoperative indocyanine green fluorescence angiography for blood flow assessment: first experience in 30 patients", published in Neurosurgery 70, 65-73; discussion 73-74 DOI: 10.1227/NEU.0b013e31822f7d7c. (2012).

An article by Feng, P., Wang, J., Wei, B. and Mi, D., titled: "A fusion algorithm for GFP image and phase contrast image of *Arabidopsis* cell based on SFL-contourlet transform", published in Comput. Math. Methods Med. 2013, 635040 DOI:10.1155/2013/635040. (2013).

An article by Schindelin, J. et al., titled: "Fiji: an open-source platform for biological-image analysis", published in Nat. Methods 9, 676-682 DOI: 10.1038/nmeth.2507 (2012).

An article by Engel, O., Kolodziej, S., Dirnagl, U. and Prinz, V., titled: "Modeling stroke in mice—middle cerebral artery occlusion with the filament model", published in J. Vis. Exp. JoVE DOI: 10.3791/2423. (2011).

An article by Ian. R. Winship, titled "Laser Speckle Contrast Imaging to Measure Changes in Cerebral Blood Flow", published "Methods in Molecular biology", Volume 1135, 2014, pp 223-235.

An article by Heling Zhou, Kate Luby-Phelps, Bruce E. Mickey, Amyn A. Habib, Ralph P. Mason, and Dawen Zhao, titled: "Dynamic near-infrared optical imaging of 2-deoxyglucose uptake by intracranial glioma of athymic mice", published in PloS One, November 2009, Volume 4, Issue 11.

An article by Li P, Ni S Zhang, Zeng and Luo Q titled: "Imaging cerebral blood flow through the intact rat skull with temporal laser speckle imaging", published in Optics letters, 2006, 15:31 (12)1824-1826.

An article by Nikos Koutsias, Michael Karteris and Emilio Chuvieco titled: "The Use of Intensity-Hue-Saturation Transformation of Landsat-5 Thematic Mapper Data for Burned Land Mapping", published in Photogrammetric Engineering & Remote Sensing Vol. 66, No. 7, July 2000, pp. 829-839.

An article by G. Benndorf titled: "Color-Coded Digital Subtraction Angiography: The End of a Monochromatic Era?" published in AJNR Am J Neuroradiol 31:925-27, May 2010.

An article by P. Gölitz, •T. Struffert, •H. Lücking, •J. Rösch, •F. Knossalla, •O. Ganslandt, •Y. Deuerling-Zheng and •A. Doerfler titled: "Parametric Color Coding of Digital Subtraction Angiography in the Evaluation of Carotid Cavernous Fistulas", published in Clin Neuroradiol (2013) 23:113-120, DOI 10.1007/s00062-012-0184-8.

The disclosures of all references mentioned above and throughout the present specification, as well as the disclosures of all references mentioned in those references, are hereby incorporated herein by reference.

SUMMARY OF THE INVENTION

A method is described for vascular imaging through an intact skull of a mouse which combines laser speckle imaging and fluorescent imaging with dynamic color mapping and image fusion. A wide-field image generated by a method described presents clear visual information on blood vessels, blood flow and perfusion in the cerebral cortex and meninges of the mouse. This simple, robust and inexpensive method has a potential of becoming an important tool for assessment of brain hemodynamics.

According to an aspect of some embodiments of the present invention there is provided a method of transcranial brain optical imaging including obtaining a Laser Speckle (LS) image of cranial blood vessels of a subject, obtaining a Dynamic Fluorescence (DF) image of the cranial blood vessels of the subject, and combining the LS image and the DF image producing a combined color image which displays both structure of the cranial blood vessels and perfusion of blood along the cranial blood vessels.

According to some embodiments of the invention, the perfusion is displayed in the combined color image as color coding of a structure of the cranial blood vessels.

According to some embodiments of the invention, the structure of the cranial blood vessels is displayed as Intensity in the combined color image and the perfusion is displayed as Hue in the combined color image.

According to some embodiments of the invention, the perfusion of blood is displayed based, at least in part, on the DF image.

According to some embodiments of the invention, the structure of the cranial blood vessels is displayed based, at least in part, on the DF image.

According to some embodiments of the invention, a plurality of DF images are obtained at different times.

According to some embodiments of the invention, different DF images obtained at different times are displayed as different colors in the combined color image.

According to some embodiments of the invention, a value of the different colors along a color axis corresponds to a time of obtaining the DF image along a time axis.

According to some embodiments of the invention, the combined color image is produced by combining values from the LS image and the DF image into a value in the IHS color space.

According to some embodiments of the invention, the structure of the cranial blood vessels is displayed as Intensity and the perfusion of fluorescent material along the cranial blood vessels is displayed as Hue.

According to some embodiments of the invention, the structure of the cranial blood vessels is displayed as Saturation and the perfusion of fluorescent material along the cranial blood vessels is displayed as Hue.

According to some embodiments of the invention, a Hue value of a pixel in the combined color image corresponds to a value of a corresponding pixel in the LS image. According to some embodiments of the invention, an Intensity value of a pixel in the combined color image corresponds to a value of a corresponding pixel in the DF image.

According to some embodiments of the invention, a value of a pixel in the combined color image corresponds to a transformation of a value of a corresponding pixel in the LS image and a corresponding pixel in the DF image into a rotated IHS color space.

According to some embodiments of the invention, the combined color image is produced by combining values from the LS image and the DF image into a value in the IHS color space, and in which, for each pixel in the combined color image: setting an Hue value of the pixel in the combined image based, at least in part, on a value of a corresponding pixel in the LS image, and setting an Intensity value of the pixel in the combined color image based, at least in part, on a time of obtaining the DF image along a time axis.

According to some embodiments of the invention, the subject of the transcranial brain optical imaging is a mouse. According to some embodiments of the invention, the subject of the transcranial brain optical imaging is a subject having a cranium thickness of less than 0.25 millimeters. According to some embodiments of the invention, the LS image and the DF image are captured through a non-thinned cranium.

According to some embodiments of the invention, the LS image and the DF image are captured through an intact skin.

According to some embodiments of the invention, further including removing hair from a scalp over a cranium of the subject prior to obtaining the images of the cranial blood vessels of the subject.

According to some embodiments of the invention, further including applying a liquid to a clear scalp produced by the removing the hair. According to some embodiments of the invention, further including applying a mixture of glycerol and liquid paraffin oil to a clear scalp produced by the removing the hair.

According to some embodiments of the invention, the LS image and the DF image are captured following craniotomy. According to some embodiments of the invention, the LS image and the DF image are captured through an open fontanel of a baby in the first months of life.

According to some embodiments of the invention, further including obtaining a plurality of the LS images of the cranial blood vessels of the subject at different times, and calculating a heart rate of the subject of the transcranial brain optical imaging based, at least in part, on a rate of a varying of intensity of the plurality of the LS images.

According to some embodiments of the invention, further including calculating a blood flow rate based, at least in part, on differences between the plurality of DF images.

According to some embodiments of the invention, further including obtaining a plurality of the LS images of the cranial blood vessels of the subject at different times, calculating a heart rate of the subject of the transcranial brain optical imaging based, at least in part, on a rate of a varying of intensity of the plurality of the LS images, obtaining a plurality of the DF images of the cranial blood vessels of the subject at different times, calculating a blood flow rate based, at least in part, on differences between the plurality of the DF images, and comparing the heart rate to the blood flow rate.

According to an aspect of some embodiments of the present invention there is provided a method for producing a medical image which displays change of a medical subject over time including obtaining a first medical image of the medical subject, obtaining a second medical image of the medical subject, and producing a combined color image based on the first medical image and the second medical image wherein, for each pixel in the first medical image: setting an Intensity value of the pixel in the combined color image based, at least in part, on a value of a corresponding pixel in the first medical image, and setting a Hue value of the pixel in the combined color image based, at least in part, on a difference between the value of the corresponding pixel in the first medical image and the value of the corresponding pixel in the second medical image.

According to some embodiments of the invention, the obtaining a second medical image of the medical subject includes obtaining a sequence of medical images of the medical subject, and producing a MIP (Maximum Intensity Projection) image based on the sequence of medical images of the medical subject, and the setting a Hue value of the pixel in the combined color image includes setting a Hue value of the pixel in the combined color image based on a time of obtaining the MIP image along a time axis.

According to an aspect of some embodiments of the present invention there is provided a method for producing a medical image including producing a plurality of raw LS images, producing an LS image of blood vessels based, at least in part, on the plurality of raw LS images, calculating a velocity distribution of blood in blood vessels based, at least in part, on the plurality of raw LS images, producing a plurality of DF images, producing a DF image of blood arteries based, at least in part, on the plurality of DF images, calculating a velocity distribution of blood in arteries based, at least in part, on the plurality of DF images, producing a DF image of blood veins based, at least in part, on the plurality of DF images, calculating a velocity distribution of blood in veins based, at least in part, on the plurality of DF images, producing a fused, or combined, color coded image of arteries and veins, including blood flow velocity indications, based, at least in part, on the velocity distribution of blood in arteries and the velocity distribution of blood in veins.

According to an aspect of some embodiments of the present invention there is provided apparatus for transcranial brain optical imaging including a laser for laser illumination of a subject of transcranial brain optical imaging, a lamp for exciting fluorescence in the subject of transcranial brain optical imaging, and an optic system for collecting light from the subject of the transcranial brain optical imaging to a camera for capturing transcranial brain optical images, and a camera for capturing transcranial brain optical images from the optic system, wherein the optic system includes a common optical path for both laser light scattered from the subject and fluorescent light emitted from a fluorescent dye excited by the lamp for exciting fluorescence.

According to some embodiments of the invention, further including an optical filter in the optical path of the optical system for passing light in a wavelength of the laser. According to some embodiments of the invention, further including an optical filter in the optical path of the optical system for passing light in a wavelength of the fluorescent light.

According to some embodiments of the invention, further including a filtering component in the optical path of the optical system configured to exchange between an optical filter for passing light in a wavelength of the laser and an optical filter for passing light in a wavelength of the fluorescent light.

According to an aspect of some embodiments of the present invention there is provided a method of comparing heart rate to blood flow rate including obtaining a plurality of LS (Laser Speckle) images of blood vessels of a subject at different times, calculating a heart rate of the subject based, at least in part, on a rate of a varying of intensity of the plurality of the LS images, obtaining a plurality of DF (Dynamic Fluorescence) images of the subject at different times, calculating a blood flow rate based, at least in part, on differences between the plurality of the DF images, and comparing the heart rate to the blood flow rate.

According to an aspect of some embodiments of the present invention there is provided a method of monitoring brain development over time through an open fontanel in the first months of life including (a) obtaining a Laser Speckle (LS) image of cranial blood vessels through an open fontanel of a subject, (b) obtaining a Dynamic Fluorescence (DF) image of the cranial blood vessels through the open fontanel of the subject, (c) combining the LS image and the DF image producing a first combined color image which displays both structure of the cranial blood vessels and perfusion of blood along the cranial blood vessels, (d) repeating (a)-(c) over time to monitor brain development over time.

According to some embodiments of the invention, the repeating (a)-(c) over time includes repeating (a)-(c) even when the fontanel starts to close. According to some embodiments of the invention, the repeating (a)-(c) over time includes repeating (a)-(c) even after the fontanel has closed.

According to an aspect of some embodiments of the present invention there is provided a method of monitoring brain emboli over time including (a) obtaining a Laser Speckle (LS) image of cranial blood vessels of a subject, (b) obtaining a Dynamic Fluorescence (DF) image of the cranial blood vessels of the subject, (c) combining the LS image and the DF image producing a first combined color image which displays both structure of the cranial blood vessels and perfusion of blood along the cranial blood vessels, (d) repeating (a)-(c) over time to monitor development of brain emboli over time.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 1A is a simplified illustration of an experimental setup and an image processing flow, both according to example embodiments of the invention;

FIG. 1B is a simplified illustration of an experimental setup and an image processing flow according to another example embodiment of the invention;

FIG. 1C is a simplified illustration of an image processing flow according to yet another example embodiment of the invention;

FIG. 2A is a simplified illustration of images produced by a TOVI (Transcranial Optical Vascular Imaging) system according to an example embodiment of the invention;

FIG. 2B is a simplified illustration of Hybrid DFLS images produced using transformations into a color space at various rotations of a color space axes according to an example embodiment of the invention;

FIG. 3A is a set of four images depicting examples of LS images produced according to an example embodiment of the invention;

FIG. 3B is a set of four images depicting additional examples of images produced according to an example embodiment of the invention;

FIG. 4A depicts DF images and a graph produced according to an example embodiment of the invention;

FIG. 4B depicts DF images and a graph produced according to yet another example embodiment of the invention;

FIG. 5A is a simplified flowchart illustration of combining a stack of raw LS images into a resultant computed LS image according to an example embodiment of the invention;

FIG. 5B is a simplified flowchart illustration of determining physiological information using LS images according to an example embodiment of the invention;

Figure 6:
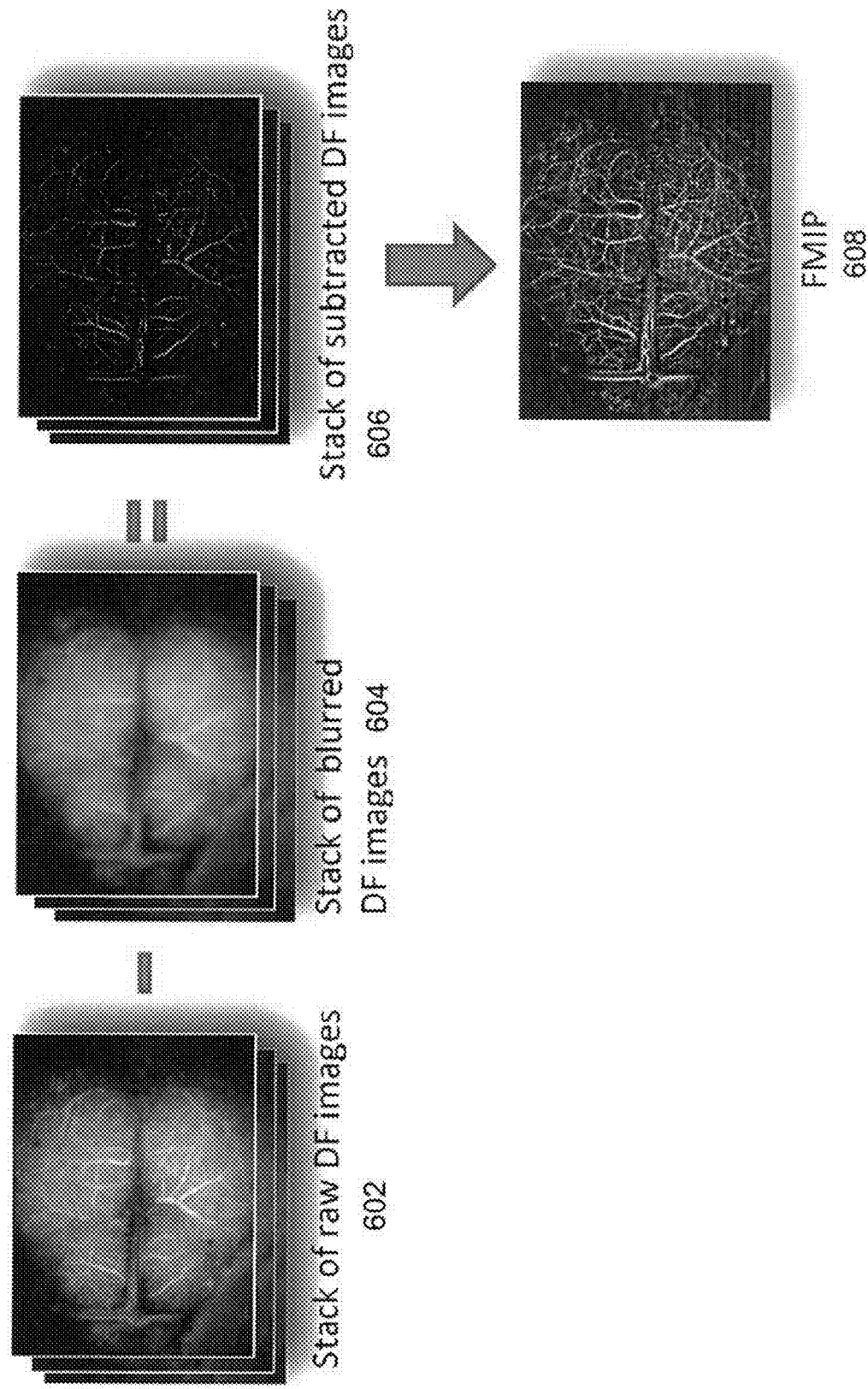
Figure 7:
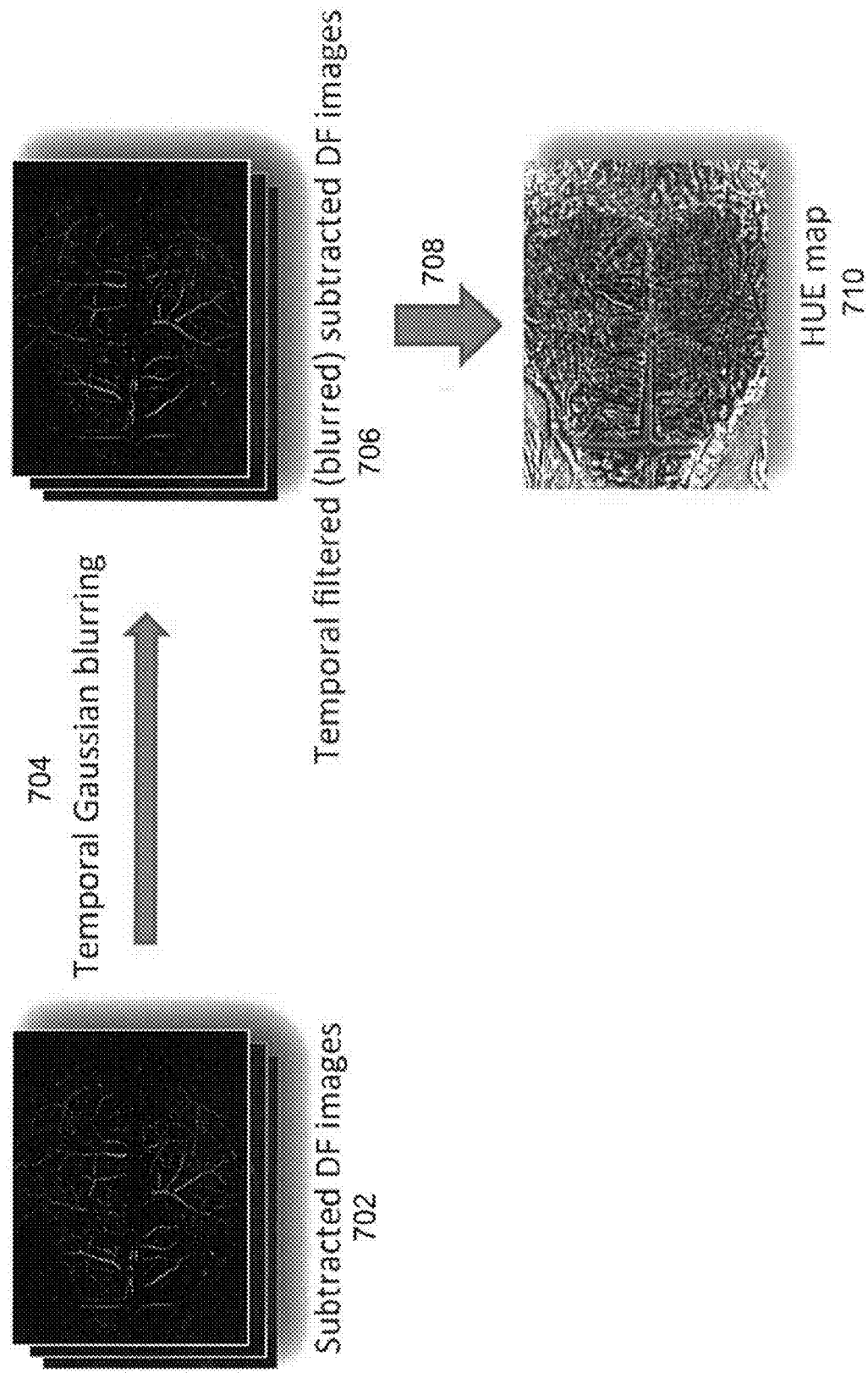
Figure 8:
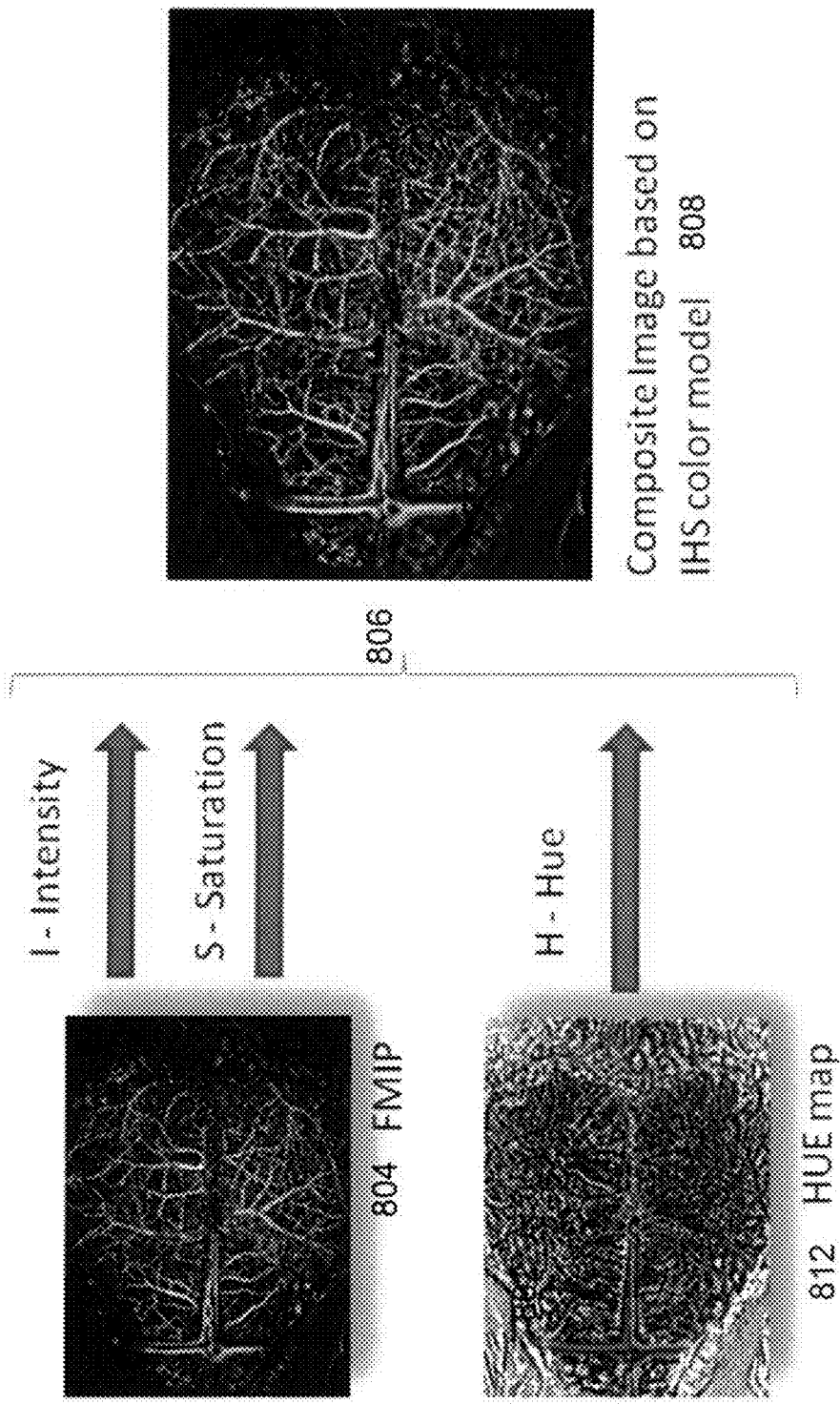
Figure 9:
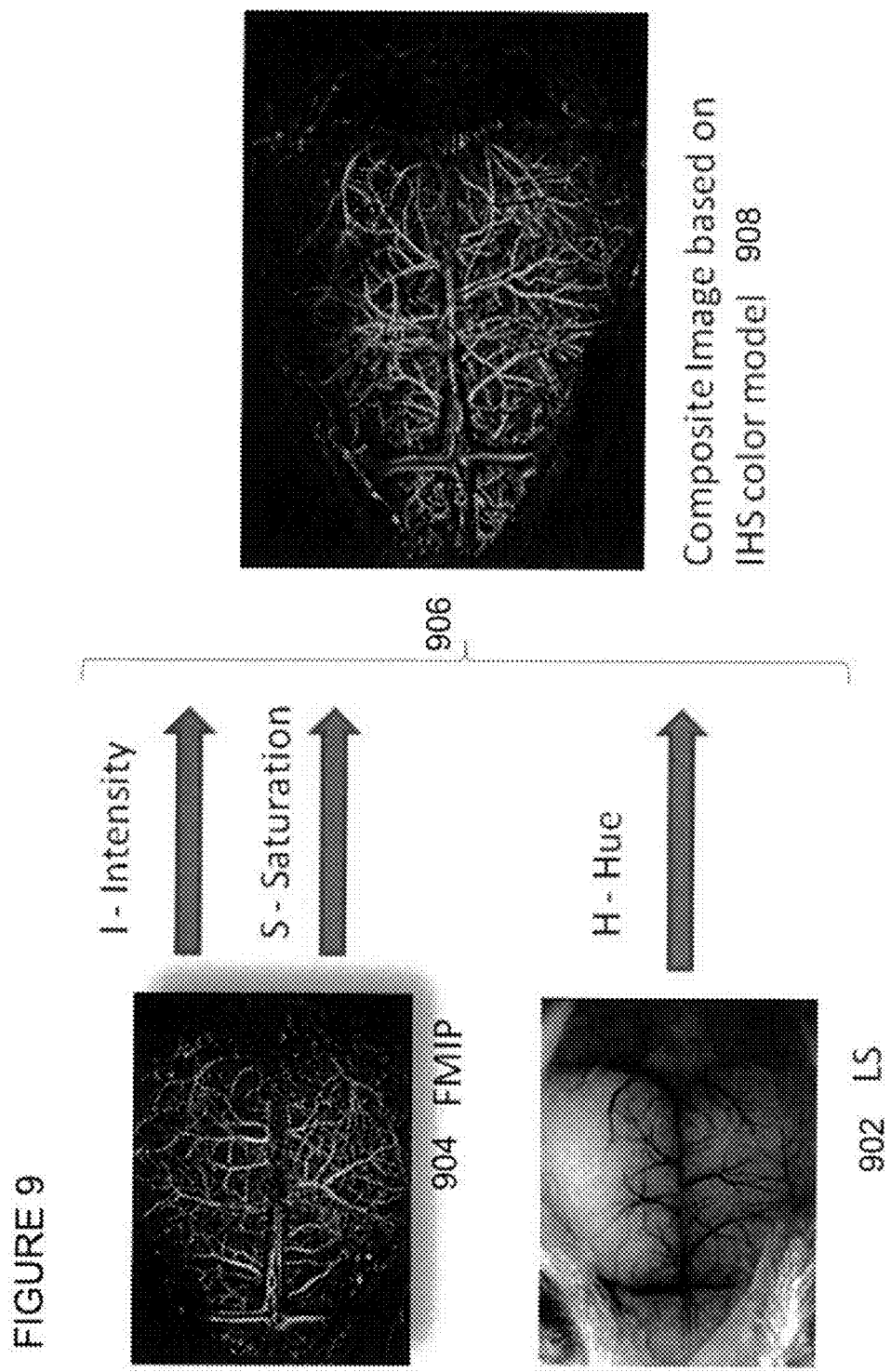
Figure 10:
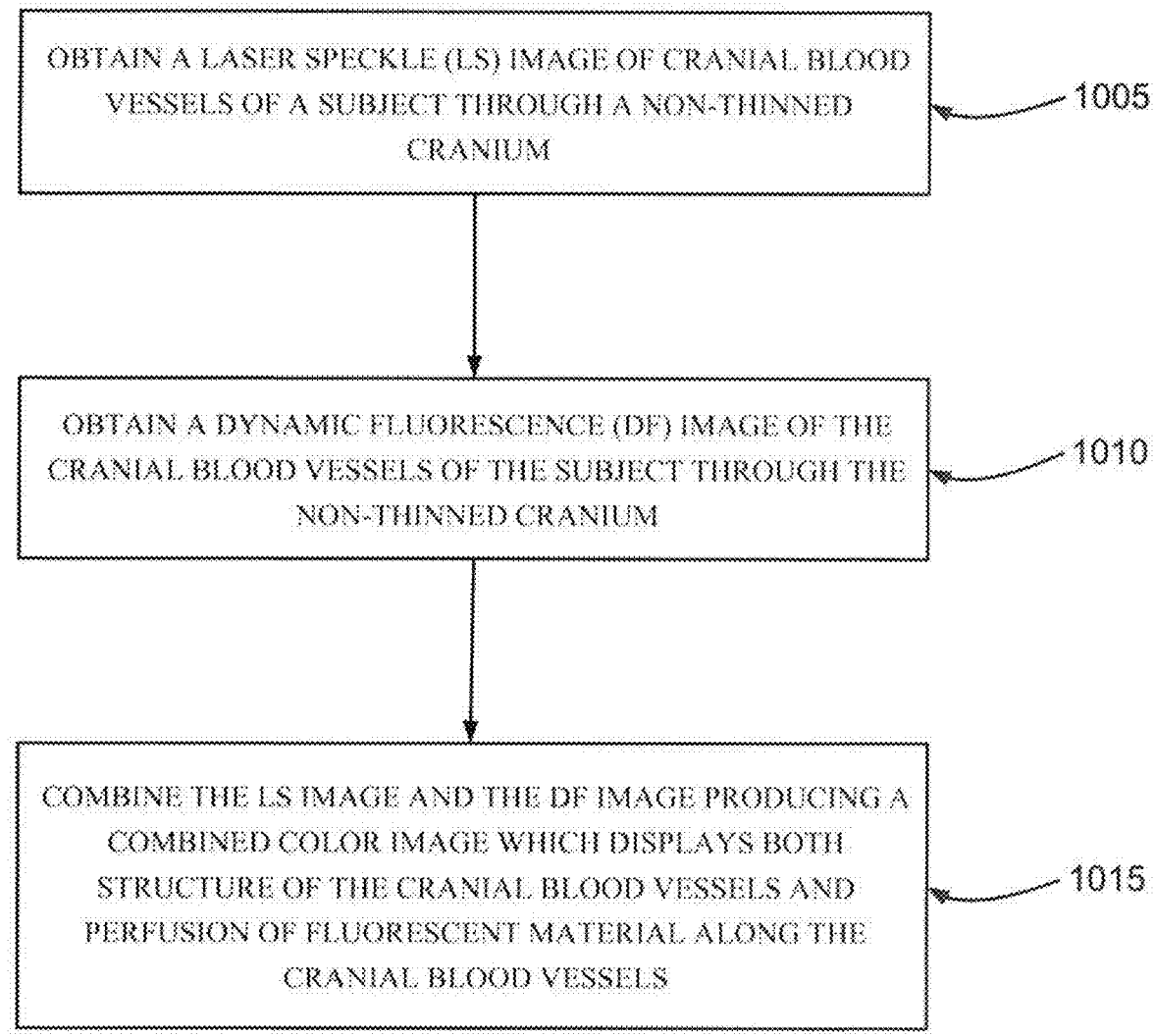
Figure 11:
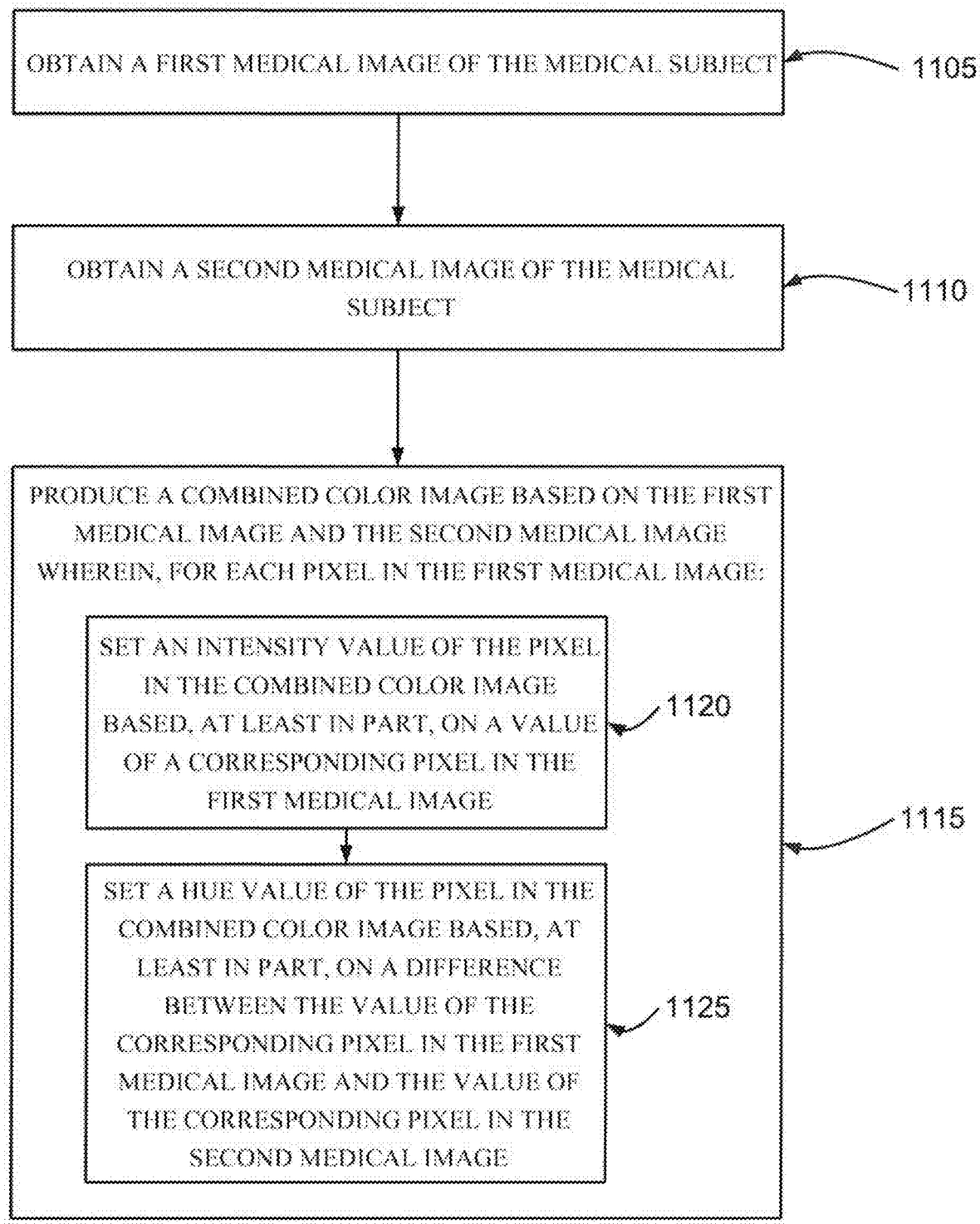
Figure 12:
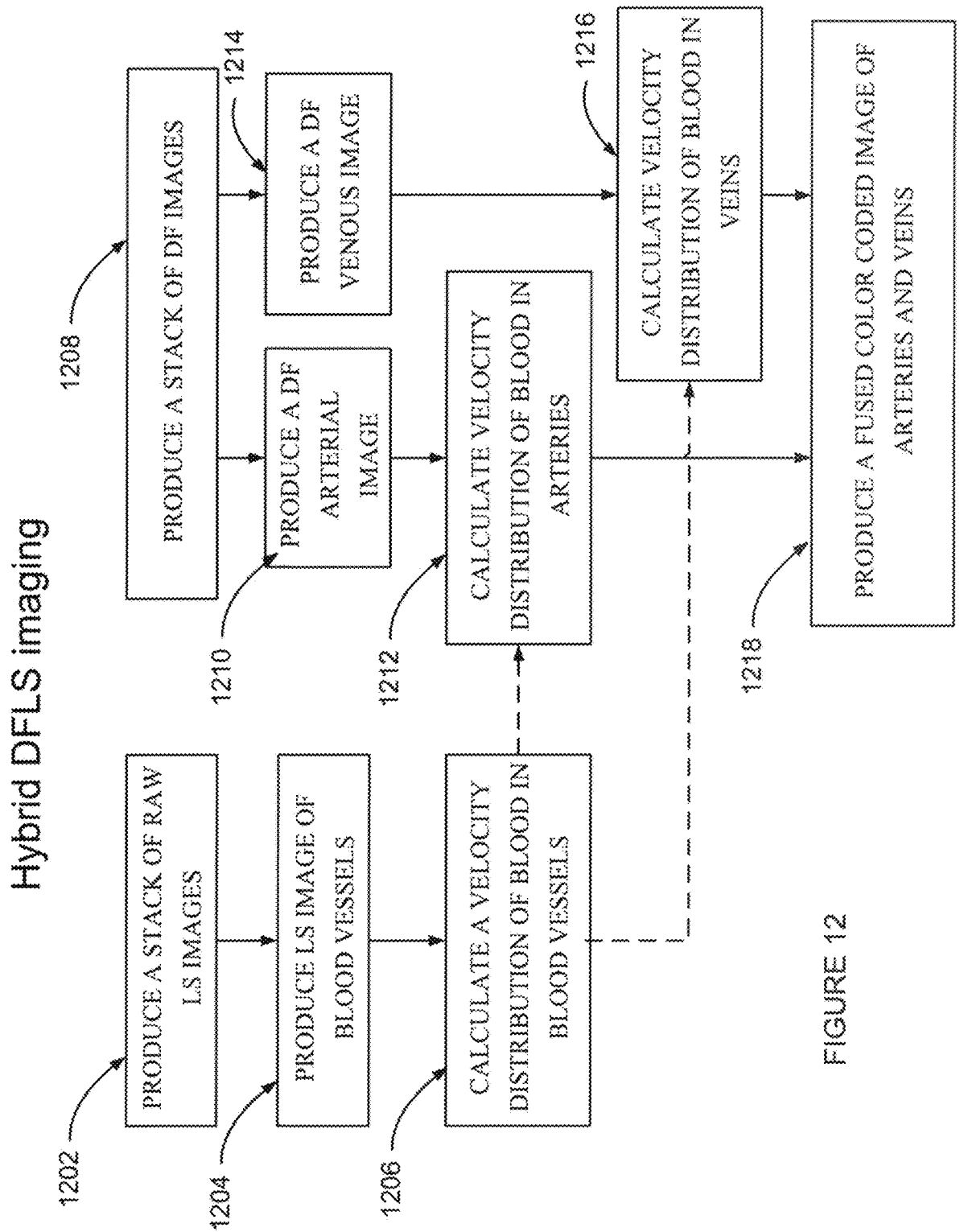

FIG. 6 is a simplified flowchart illustration of computing a filtered MIP (Maximum Intensity Projection) image from a stack of raw DF images according to an example embodiment of the invention;

FIG. 7 is a simplified flowchart illustration of a generation of a HUE map from subtracted DF images according to an example embodiment of the invention;

FIG. 8 is a simplified flowchart illustration of a generation of a color composite image based on an IHS color model according to an example embodiment of the invention;

FIG. 9 is a simplified flowchart illustration of a generation of a color composite image based on an IHS color model according to another example embodiment of the invention;

FIG. 10 is a simplified flowchart illustration of a method of transcranial brain optical imaging according to an example embodiment of the invention;

FIG. 11 is a simplified flowchart illustration of a method for producing a medical image which displays change of a medical subject over time according to an example embodiment of the invention; and FIG. 12 is a simplified flowchart illustration of a method for producing a medical image by hybrid DFLS imaging according to an example embodiment of the invention.

DESCRIPTION OF SPECIFIC EMBODIMENTS OF THE INVENTION

The present invention, in some embodiments thereof, relates to systems and methods for transcranial brain imaging and, more particularly, but not exclusively, to systems and methods for Transcranial Optical Vascular Imaging (TOVI) of cortical hemodynamics in mouse brain, and, even more particularly, but not exclusively, to displaying the imaging results.

A Short Overview

An aspect of some embodiments of the invention relates to transcranial brain optical imaging performed on a mouse.

Brain optical imaging has been done using various techniques, as described above in the Background section. However, a piece of a skull has typically been taken off a subject, in order to perform optical imaging. Imaging through a skull is difficult, because the skull diffuses whatever imaging technique is used, often to a point where it was not practical. The inventors have discovered that optical imaging may be performed through a mouse skull and produce acceptable resolution.

An aspect of some embodiments of the invention relates to transcranial brain optical imaging performed on a mouse. Various medical trials, for example pre-clinical trials of medical procedures and/or medications, may be performed on a mouse brain rather than a rat brain or a brain of some other thicker skulled animal. Using the thinner skulled mouse potentially enables performing the trials at less injury to a mouse, potentially enables reusing mice, potentially lowers expenses, and potentially decreases effort of running the trials.

In some embodiments, the subject of transcranial imaging is selected so that thickness of the skull of the subject is at or below 250 micrometers (0.25 mm). In some embodiments, the skull of the subject of transcranial imaging is thinned so that thickness of the skull of the subject is at or below 250 micrometers (0.25 mm). In some embodiments a mouse under an age of approximately 6 months is used. In some embodiments, the thickness of the skull is higher than 250 micrometers. It is noted that any thickness of the skull of the subject between 0 and 250 micrometers is included in the range "at or below 250 micrometers".

In some embodiments the thickness of the skull is higher than 250 micrometers, such as 300 micrometers, 500 micrometers and 1 millimeter, and one or more Near Infra Red fluorescent probe materials, emitting radiation at 700 to 1300 nm wave lengths, are used.

In some embodiments, Transcranial Optical Vascular Imaging (TOVI) is performed through an open fontanel, or TOVI is performed through a thin skull, at a first time, and an initial map, or image, of the blood vessels is optionally produced. At a later time a subsequent TOVI is optionally performed through a thicker skull of the same subject, who may be older and have a thicker skull. The first image of the blood vessels is optionally merged with the subsequent images produced through the thicker skull, potentially improving the subsequent TOVI. Such embodiments potentially enable monitoring blood vessels through a thicker skull than possible without having the initial image.

An aspect of some embodiments of the invention relates to transcranial brain optical imaging performed using Laser Speckle Imaging (LSI). In some embodiments, several laser speckle images are taken, and subtraction images are produced between subsequent images. The subtraction images can enhance visibility of areas where image intensity changed between the subsequent images. For example, without limiting generality, when the laser used is of a wavelength which interacts with blood, a change in blood flow caused by the pulse can cause the blood vessels to appear enhanced. In some embodiments transcranial brain LS imaging is used to image a structure of blood vessels in the brain. A potentially useful aspect of producing LS images is that the images do not require injection of a contrast dye and that a lack of perfusion in blood vessels, for example caused by an occlusion in a blood vessel, reduces the contrast and/or detail or even completely hides the occluded blood vessel in a LS image.

An aspect of some embodiments of the invention relates to transcranial brain optical imaging performed using Dynamic Fluorescence (DF) imaging. In some embodiments, a DF image is made of fluorescent material injected into a blood stream, and the DF image captures a location of the fluorescent material. For example, without limiting generality, the DF image can image blood vessels, when the fluorescent material is injected into the blood stream. In some embodiments, arteries can be differentiated from veins, based on the fluorescent material appearing in arteries or in veins at different times. In some embodiments, the fluorescent material is injected into an artery, and in some embodiments the fluorescent material is injected into a vein.

The term Dynamic Fluorescent (DF) imaging is used herein for a fluorescent imaging modality, optionally a contrast enhanced fluorescent imaging modality.

The term Laser Speckle (LS) imaging is used herein for a label free imaging modality, based on dynamic light scattering obtained from, by way of a non-limiting example, moving red blood cells.

DF imaging typically provides additional information which is optionally used for attenuation correction for the Laser Speckle (LS) imaging.

In some embodiments, data extracted from a dynamic fluorescence pattern is used as a reference map for attenuation correction.

In some embodiments, a stack of DF images potentially provides detailed information about structure of blood vessels, which may be superior to an LS image.

In some embodiments, DF imaging provides high definition a-priori data about detailed microstructure of blood vessels at relatively high spatial resolution (relative to LS imaging).

In some embodiments, anatomic data obtained from DF is used to improve LS imaging performance, via attenuation correction. In some embodiments attenuation correction is optionally applied as attenuation and/or a brightening of anatomic features obtained from DF onto an LS image. In some embodiments the attenuation correction is performed on areas identified as belonging to anatomic features. In some embodiments attenuation is performed pixel-by-pixel.

In some embodiments, anatomic data obtained from DF is used to improve LS imaging performance, via uncertainty correction. In cases where, by way of a non-limiting example, fluorescence gives a partial image or a disturbed area within a blood vessel image, the LS image optionally provides data which improves the combination image. The opposite also holds—In cases where, by way of a non-limiting example, LS give a partial image or a disturbed area within a blood vessel image, the DF image optionally provides data which improves the combination image.

In some embodiments, accuracy of blood velocity distribution obtained via LS modality is optionally improved by co-registration with a blood vessel map optionally obtained via DF modality.

In some embodiments a LS velocity map is applied separately to arteries and to veins, potentially producing more information.

It is noted that LS typically provides a low resolution image, and it may be difficult to differentiate between an artery and a vein in an LS image, even though arteries and veins are different, and veins typically appear bigger.

In some embodiments, DF imaging is used to provide a higher resolution image, and differentiate between arteries and veins.

In some embodiments, when arteries and veins have been distinguished, an analysis of velocity, flow rate etc, is optionally performed separately for arteries and for veins, and the analysis is optionally improved by knowing reasonable ranges for values of the measured parameters.

In some embodiments, a mathematical model is used for analyzing quantitative parameters for blood flow, based on a type of blood vessel—artery or vein, which is optionally determined using DF imaging.

In some embodiments, a Hybrid DFLS imaging option is implemented by one or more of:
   (a) fusing a DF image with a LS image, optionally using any image fusion protocol;
   (b) optionally improving accuracy and performance of LS image rendering by applying corrected references using anatomical data obtained from DF image, As a result, a final LS image may have higher spatial resolution;
   (c) optionally applying a continuous or repetitive LS imaging using an a-priori registered DF image reference, optionally even in case of displacement of the object. By way of a non-limiting example, during neurosurgery ICG or Fluorescein may be injected to the circulation, a preliminary, high definition, map of blood vessels may be obtained. Arteries and veins may be separately registered. LS imaging may be performed continuously. A velocity map may take into account previously obtained and registered blood vessels.

In some embodiments, a multi-camera (multi-plane imaging) is used to increase accuracy of image registration and to obtain stereoscopic (3D) information.

In some embodiments, a Hybrid DFLS imaging option is implemented by using data obtained using LS modality, optionally assisted by near infrared lasers to resolved deep blood vessels through the cranium. In some embodiments, a fluorescent dose not necessarily provide high spatial resolution, but the dose can still clearly demonstrate a direction of blood flow.

A potentially useful aspect of producing DF images is that the images potentially correspond to a concentration of a fluorescent dye, and that a lack of perfusion in blood vessels, for example caused by an occlusion or a partial occlusion in a blood vessel, reduces blood flow downstream and potentially increases the concentration of the fluorescent dye in the occluded blood vessel in a LS image. DF images may potentially image blood vessels which are partially of completely occluded better than, for example LS images.

In some embodiments a number of DF images are taken, and a movie may optionally be constructed from the DF images. In case of injecting a fluorescent material into a blood stream, a fluorescent area, or a location of peak fluorescence, will flow with the blood flow, and the movie can display the flow.

An aspect of some embodiments of the invention relates to transcranial brain optical imaging performed using two modalities of optical imaging, and producing a resultant image which is a combination of images from the two modes.

In some embodiments of combining images, using the non-limiting example of imaging blood flow, an LS image may be produced, potentially showing structure of blood vessels, and potentially showing areas of full or partial occlusion. A DF image may optionally be combined with the LS image, showing a location of fluorescent material. A DF movie may be combined with the LS image showing temporal change in the location of fluorescent material, thereby showing perfusion of blood in the blood vessels. The combination potentially enhances understanding of the medical image, by potentially highlighting an occluded area, as may also be viewed in a LS-only image, together with perfusion information as may also be viewed in a DF-only image.

In some embodiments, a combined image may replace the DF movie, or a portion of the DF movie, using a color mapping to display the passage of time along the movie. The combined image optionally shows the location of the fluorescent material at different times along the movie as different colors.

A potentially useful aspect of producing a hybrid image combining LS and DF images is that the hybrid image potentially displays, in one image, the occluded blood vessels brought out by the DF imaging, information about perfusion in the occluded blood vessels brought out by the DF imaging, while also emphasizing the occluded areas brought out by the LS imaging.

Another potentially usefully property of using both LS imaging and DF imaging in hemodynamic trials is that the LS imaging may be performed continuously, allowing a tracking of the subject until it is decided to administer a fluorescent dye, and optionally perform DF imaging.

A potentially useful aspect of the experimental setup described below with reference to FIG. 1A is that LS imaging and DF imaging may be performed through the same optical path, and do not require changing component when transferring from LS imaging to DF imaging.

In some embodiments, LS imaging and DF imaging are performed simultaneously.

In some embodiments, the two modalities are combined to produce a color image, where the color image is constructed using the IHS (Intensity, Hue, Saturation) model of color, or the HSV (Hue, Saturation, brightness Value) model of color. In some embodiments, the color image is constructed such that a first modality of optical imaging contributes data to the Intensity or Saturation values of the color image, and a second modality of optical imaging contributes data to the Hue values of the color image.

The inventors have developed a two-modality combination color image which is useful in conveying cortical hemodynamics to a viewer.

In some embodiments, the two modalities are Laser Speckle Imaging (LSI) and Dynamic Fluorescent (DF) imaging.

An aspect of some embodiments of the invention relates to physiological parameters relating to a subject being measured using transcranial brain optical imaging. By way of a non-limiting example, LSI is optionally used to measure intensity/velocity of blood flow, and calculate the subject's heart rate based on the measurement.

In some embodiments an LSI signal is taken from a number n of LSI frames, and fluctuation of intensity of the signal is optionally measured. The fluctuation correlates with the pulse. In some embodiments, optionally according to the Nyquist principle, the frame rate used for calculating the pulse is higher than the expected pulse. Calculating the heart rate potentially provides additional information relevant to a trial, using the setup used for the optical imaging, without requiring an additional heart rate monitor. The heart rate may also be relevant to performing a trial. By way of a non-limiting example, the heart rate may also be relevant to performing the Dynamic Fluorescent imaging and/or to calculating a blood flow rate, which may be dependent on a calculated heart rate.

The method described herein with reference to some embodiments of the invention, simplifies transcranial vascular imaging, for example in preclinical studies. The method is named Transcranial Optical Vascular Imaging (TOVI).

In some embodiments, the imaging operates through a cranial thickness of up to 250 µm and can therefore be used transcranially, for example in mice, for example mice under an age of 6 months.

In some embodiments, because the skull remains intact, there is no injury to the meninges or underlying brain tissues and the unperturbed cortical circulation of an animal can be followed through entire experiments.

In some embodiments, TOVI is based on combining two optical modalities, namely laser speckle and fluorescence imaging.

In some embodiments the combination of the two optical modalities is optionally followed by computer-assisted dynamic color mapping of acquired data.

Laser speckle imaging (LS), also known as laser speckle contrast imaging, is a technique used to visualize the vasculature, blood flow and perfusion in various biomedical applications, including imaging of major brain vessels. The LS imaging modality, which is based on dynamic scattering of diffusively reflected laser light, can be used to measure movement of red blood cells inside vessels and is therefore optionally used, in some embodiments, for continuous imaging of blood flow dynamics.

Dynamic Fluorescent imaging, referred to hereafter as DF, is a modified version of fluorescence angiography, which is used in many biomedical applications, especially in ophthalmology. The DF imaging modality follows a temporal distribution and redistribution of a fluorescent material through vasculature, and provides information about hemodynamics.

In some embodiments, following acquisition by two modalities such as LSI and DF mentioned above, images are color-coded using the IHS (intensity, hue, saturation) color model, which is typically used in computer vision.

In some embodiments, computer-assisted dynamic color mapping of DF data is optionally applied to enhance the visibility of blood vessels, facilitate distinction between cerebral arteries, cerebral veins and cranial vessels, and enable assessment of perfusion level and vascular permeability and detection of flow abnormalities.

In some embodiments, color-coded hybrid images combine data acquired by both DF and LS to clearly present information on cerebral perfusion, enabling a viewer to identify and analyze aberrations.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Introduction

Detailed non-invasive imaging of vascular network of arteries through capillaries to veins is a goal in neuroimaging, as well as for various clinical and preclinical brain-related studies, and in development of new drugs for stroke treatment.

A cerebrovascular accident (stroke) most commonly affects the middle cerebral artery (MCA). The MCA is one of the largest vessels in the brain which supplies blood to most of the outer convex brain surface and basal ganglia. Therefore, in vivo quantitative imaging of MCA and cerebral vascular network is vital for clinicians and medical researchers alike.

Over the last decade much attention has been given to optical-based imaging modalities; optical coherence tomography (OCT) and photo-acoustic tomography (PAT) have been applied for visualization of skin vascular network. Compared to modalities traditionally used for brain imaging, such as magnetic resonance angiography and X-ray computed tomography, example embodiments of optical imaging techniques described herein are portable, cost effective and are able providing higher temporal resolution.

Optical imaging has been successfully used in the small-animal stroke modeling studies. This as well as two-, multi-photon and fluorescence-based imaging modalities are seriously limited due to a high scattering of skull and skin tissues. To avoid this limitation a surgical removal of skin and skull is used to obtain high contrast images of organization of cortical map and/or brain vascular network. Thus, it has been accepted for a number of years that non-invasive optical imaging of brain (i.e. through-skull and through-skin) by using fluorescence probes is impossible.

Some embodiments of the invention produce results which demonstrate that optionally utilizing fast image acquisition a dynamic fluorescence (DF) imaging of mouse Cerebral Blood Vessels (CBVs) potentially allows demarcation of arteries and veins and clear perception of different blood vessels. Optional color coding potentially enhances visibility of CBVs and potentially enables to evaluate complex cerebral hemodynamic patterns, making this approach a practical tool for non-invasive measurement of the MCA's blood flow rate.

An Experimental Setup of an Example Embodiment

Reference is now made to FIG. 1A, which is a simplified illustration of an experimental setup and an image processing flow, both according to example embodiments of the invention.

The example embodiment of the experimental setup includes a fluorescent microscope 101; a camera 102, optionally an emission filter 109, optionally a charge-coupled device (CCD) camera; a laser source 103 with an optional diffuser 104; a fluorescent illumination source 105, such as, by way of a non-limiting example, a mercury lamp; and an imaging subject 107 holder, such as a mouse holder 106 with an optional warming plate.

In some embodiments, both the LS and DF imaging modalities use the same lens 107, optical path 108, emission filter 109 and camera 102.

In some embodiments, the emission filter 109 is switched between imaging LS images and imaging DF images, so the emission filter 109 suits the laser and/or the fluorescent light.

It is noted that the animal experiments were conducted in accordance with the regulations of the Institutional Animal Care and Use Committee (IACUC) at the Weizmann Institute.

In some embodiments an anesthetized subject, for example a mouse, is placed inside the mouse holder 106, optionally with the optional warming plate set to maintain a body temperature, for example at 37 C.

In some embodiments, a fluorescent zoom stereomicroscope SZX12 RFL2 by Olympus, Japan, is used, optionally coupled with a charge coupled device (CCD) camera Pixelfly QE, 12 bit by PCO, Germany.

In some embodiments, the mercury lamp used was a mercury short-arc discharge lamp and an emission filter was also optionally used.

In some embodiments, for image acquisition in laser speckle (LS) mode, a diode laser module LDM808/3LJ, 808 nm, 3 mW (Roithner Lasertechnik, Austria) is used, optionally coupled with an optical diffuser. A coherent laser beam optionally passes through an optional ground grass diffuser by Thorlabs, Newton, N.J., USA, to illuminate the mouse skull. Optionally the laser illuminator is placed near the mouse skull at an angle of approximately 45° for oblique illumination.

Optionally, laser speckle images are captured by the Pixelfly QE camera at, by way of a non-limiting example, 10 ms exposure time. Optionally the captured images are saved as a raw stacked 16-bit tiff files on a PC-based workstation, optionally using CamWare software, by PCO, Germany, for camera control and image acquisition.

It is noted that the term "stack of images" is used in the specification and claims to indicate two or more images, for example 2, 5, 10, 50, 100, 200, 400, 600, 1,000, or even a thousand or tens of thousands of images. While many examples of stacks with more than a hundred images are provided, the stack of images may be only two images and still be used to extract potentially useful data, such as flow velocity by comparing images, and such as image averaging to reduce noise, and other similar inter-image operations.

FIG. 1A also depicts an overview of an example embodiment of a process flow for processing images captured from the example experimental setup depicted in FIG. 1A. Further example embodiments of process flow will be described later with reference to further Figures described below.

In the example embodiment of the process flow depicted in FIG. 1A, a stack of raw Laser Speckle (LS) images 110 is optionally normalized 111, and combined to produce a combined LS image 112. In an example embodiment, the stack of raw Laser Speckle (LS) images 110 included 400 frames, each of 10 ms exposure time. In the example embodiment, the stack of raw Laser Speckle (LS) images 110 was statistically processed using a macro command for Fiji developed by one of the inventors. The mathematical formula $K=\sigma/<I>$ was applied to calculate contrast in each pixel, as further described below in a section titled "LS Image rendering". In the processed image on the right, dark areas correlate with higher blood flow, corresponding with blood vessels.

In some embodiments, a stack of raw Dynamic Fluorescence (DF) images 113 is optionally acquired by the same camera, optionally having an exposure time of 50 ms each over a 20 second interval after fluorescent material administration. The stack of raw Dynamic Fluorescence (DF) images 113 is optionally color coded such that color of a resultant DF image 116 corresponds to time along a time axis, as depicted in a graph 114, producing a resultant DF image 116.

In some embodiments, an optional noise elimination procedure is performed, in which, for each pixel the frame (corresponding to a time point) of maximum intensity projection (MIP) is identified. A graph 114 shows maximum fluorescence intensity as a function of time, illustrating a difference in arrival time between arteries (red) and veins (green).

In some embodiments the resultant DF image 116 was color-coded using the IHS color model. Optionally, Hue encodes time of maximal pixel intensity, whereas MIP is optionally encoded as intensity and saturation.

In some embodiments, the resultant DF image 116 is further combined with the LS image 112, such that the resultant DF image 116 contributes an Intensity of a resultant Hybrid DFLS image 118, while the LS image 112 contributes a Hue of the resultant Hybrid DFLS image 118. Optionally, the Hue of the resultant Hybrid DFLS image 118 corresponds to a perfusion value as depicted in a HUE axis 120.

It is noted that in LS images a high level of perfusion optionally corresponds to a dark (low intensity) area. Combining such LS images as Hue with DF images as Intensity enables the Hue not to interfere with the color coding present in the DF images.

Hybrid DFLS image 118, data from both LS and DF modalities is optionally fused, with LS contrast level optionally encoded as hue and MIP levels from the DF modality encoded as intensity and saturation.

An example embodiment demonstrating a potential of the experimental setup, image capture and subsequent image processing to visualize hemodynamic changes, and particularly perturbations in cerebral blood flow during an ischemic stroke.

Figure 1B:
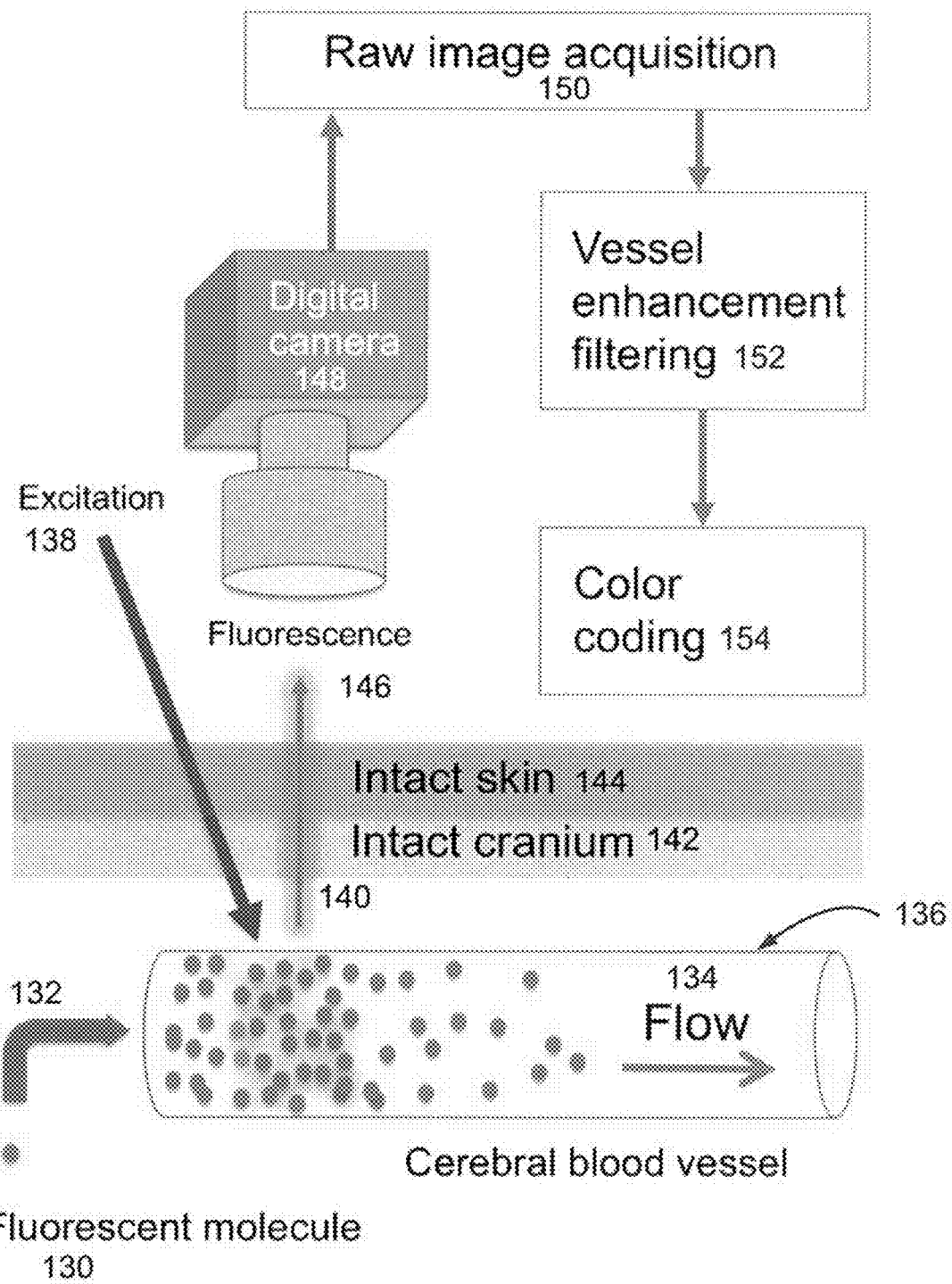

Reference is now made to FIG. 1B, which is a simplified illustration of an experimental setup and an image processing flow according to another example embodiments of the invention.

FIG. 1B depicts a schematic illustration of DF imaging system methodology: A fluorescent agent 130 is administered intravenously 132. Excitation 138 is performed, optionally by an external light source (by way of a non-limiting example excitation 720 nm, emission: 780-850 nm). The excitation 138 and emission light is passed through an optionally intact skin 144 and cranium 142, optionally after fur removal. A digital CCD camera 148 optionally records a sequence of fluorescent images 150, optionally with a 10-second interval and exposure time 45 ms. Background noise is optionally subtracted by spatial low-frequency filtering. A vessel enhancement filter is optionally applied 152 to improve visibility of blood vessels and reduce noise. Finally, color-coding is optionally used 154 to enhance perceptual visibility and distinction between arteries and veins.

Some details of DF imaging system operation are schematically shown in FIG. 1B. A standard fluorescent zoom microscope MVX-10 (Olympus, Japan) coupled with a CCD camera Pixelfly USB (PCO, Germany) were adapted for the DF imaging of mouse CBVs. The camera control and image acquisition were performed through CamWare software (PCO, Germany). A standard fluorescent illumination source was used, namely, a mercury short-arc discharge lamp. The excitation and emission wavelengths for the near-infrared (NIR) filter set were 710/50 nm and 810/90 nm (long pass), respectively.

Figure 1C:
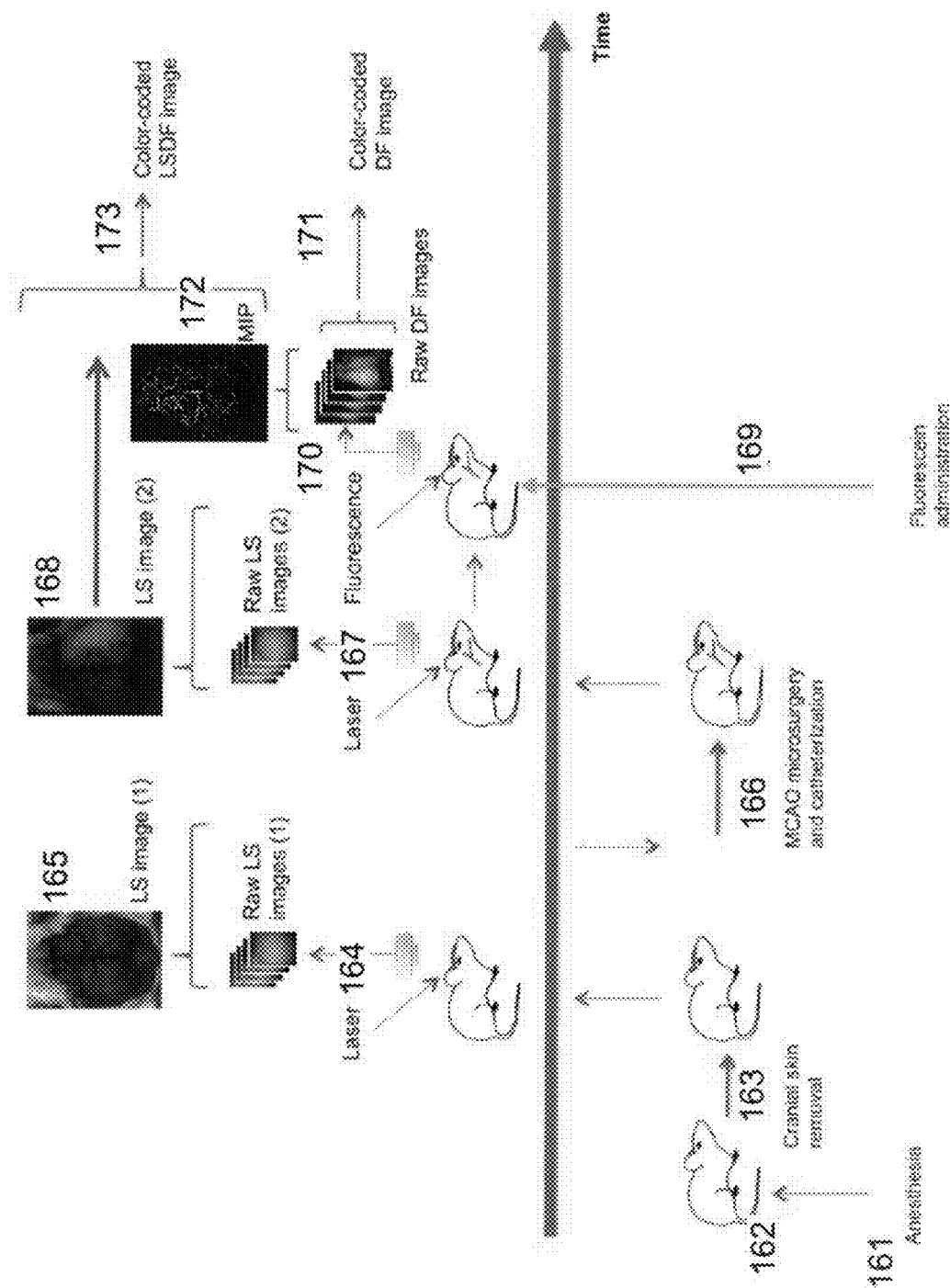

Reference is now made to FIG. 1C, which is a simplified illustration of an image processing flow according to yet another example embodiment of the invention.

FIG. 1C is a workflow chart for visualization of an example embodiment of an MCAO procedure. (161) A mouse is anesthetized (optional duration: 5 minutes). (162) The mouse is optionally placed on a thermally controlled plate (optionally for 2 minutes). (163) Cranial skin is removed from the mouse (optional duration 2 minutes). (164) Mouse is optionally placed under an imager; 400 frames of raw LS images are optionally acquired and optionally saved. (165) LS image reconstruction using LS macro is optionally performed (optional duration 10 seconds, although can be in a range between less than 1 second and more than a minute). (166) The mouse is optionally moved to a surgical plate, MCAO and catheterization of tail vein are optionally performed (optional duration 30 minutes). (167) The mouse is optionally placed under the imager; 400 frames of raw LS images are optionally acquired and optionally saved. (168) LS images are optionally reconstructed (optional duration 10 seconds, although can be in a range between less than 1 second and more than a minute) and optionally analyzed (optional duration 20 seconds) to determine a potentially successful occlusion. (169) Upon success of occlusion, fluorescein is optionally administered (optional duration 2 seconds, although can be in a range between less than 1 second and more than 10 seconds). (170) 400 frames of raw DF images are optionally acquired and optionally saved. (171) DF image reconstruction is optionally performed, optionally using a DF macro (optional duration 2 minutes). (172) A Maximum Intensity Projection (MIP) image is optionally extracted from the raw DF sequence (optional duration 10 seconds). (173) LSDF image reconstruction is optionally performed, optionally using IHS code in ImageJ/Fiji (30 seconds).

The above discussion relates to mice, however, it is noted that the techniques which are described above with reference to mice apply to other animals and to other scenarios.

For example, instead of mice, TOVI can be performed on other thin-skulled animals.

For example, TOVI can be performed on animals which have an open fontanel during the first period of their life. TOVI can be performed on human babies which have an open fontanel during the first period of their life. In some embodiments, human subject, and especially babies, are optionally given sedation and/or analgesia similarly to a treatment provided for MRI imaging so as to prevent restlessness and movement.

For example, TOVI can be performed on animals which have had a craniotomy performed.

For example, some animals do not require a heating pad to maintain body temperature.

In some embodiment, subjects of TOVI are optionally immobilized, so as to prevent movement during imaging.

Figure 2A:
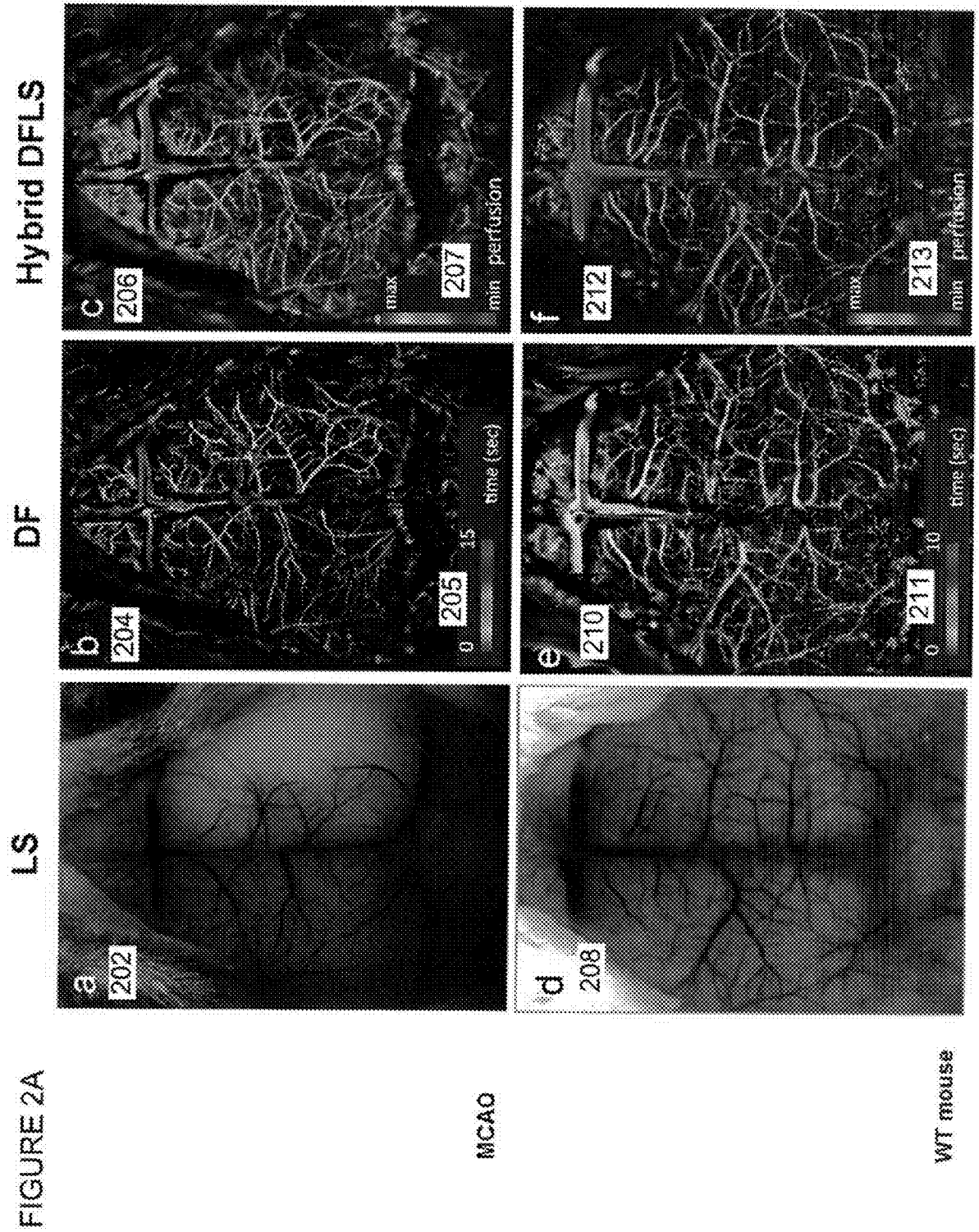

Reference is now additionally made to FIG. 2A, which is a simplified illustration of images 202 204 206 208 210 212 produced by a TOVI (Transcranial Optical Vascular Imaging) system according to an example embodiment of the invention.

In the scenario depicted by the images 202 204 206 208 210 212 of FIG. 2A, an ischemic stroke was induced by occlusion of the middle cerebral artery (MCA) of a mouse, using a filament model.

Image (a) 202 depicts an LS image of the brain of the MCA occluded mouse.

Image (b) 204 depicts a DF image of the brain of the MCA occluded mouse. Image (b) 204 also depicts a color scale used to color code the DF image (b) 210 according to a time following occlusion.

Image (c) 206 depicts a Hybrid DFLS image of the brain of the MCA occluded mouse. Image (c) 206 also depicts a color scale used to color code the Hybrid DFLS image (c) 206 corresponding to an amount of perfusion.

In some embodiments the perfusion calculation is relative and/or semi-quantitative, and does not use absolute numbers.

Images of the vasculature of an untreated control mouse are shown for comparison.

Image (d) 208 depicts an LS image of the brain of the untreated control mouse.

Image (e) 210 depicts a DF image of the brain of the untreated control mouse. Image (e) 210 also depicts a color scale used to color code the DF image (e) 210 according to a time following occlusion.

Image (f) 212 depicts a Hybrid DFLS image of the brain of the untreated control mouse. Image (f) 212 also depicts a color scale used to color code the Hybrid DFLS image (f) 212 corresponding to an amount of perfusion.

After occlusion, data is optionally collected continuously using the LS mode to identify a right moment at which to inject fluorescent material. Image (a) 202 shows the LS image acquired at the time chosen for injection.

The effect of the occlusion on perfusion in the right hemisphere is clearly seen in a dynamic color-mapped panoramic view of the vasculature obtained by DF mode, and depicted in image (b) 204. A Hybrid DFLS mode image (c) 206 demonstrates an area of lesion in the right hemisphere of the mouse brain.

It is noted that the LS images may optionally be binary-valued, such as black and white, and still display blood vessel structure and optional occlusions. In some embodiments, the LS images are binary valued, and/or use a small number of bits for a grey scale. In some embodiments the LS images use a standard number of bits for a grey scale, such as 8 or more bits. In some embodiments the LS images use as many bits as appropriate for the dynamic range of the image acquisition system.

Figure 2B:
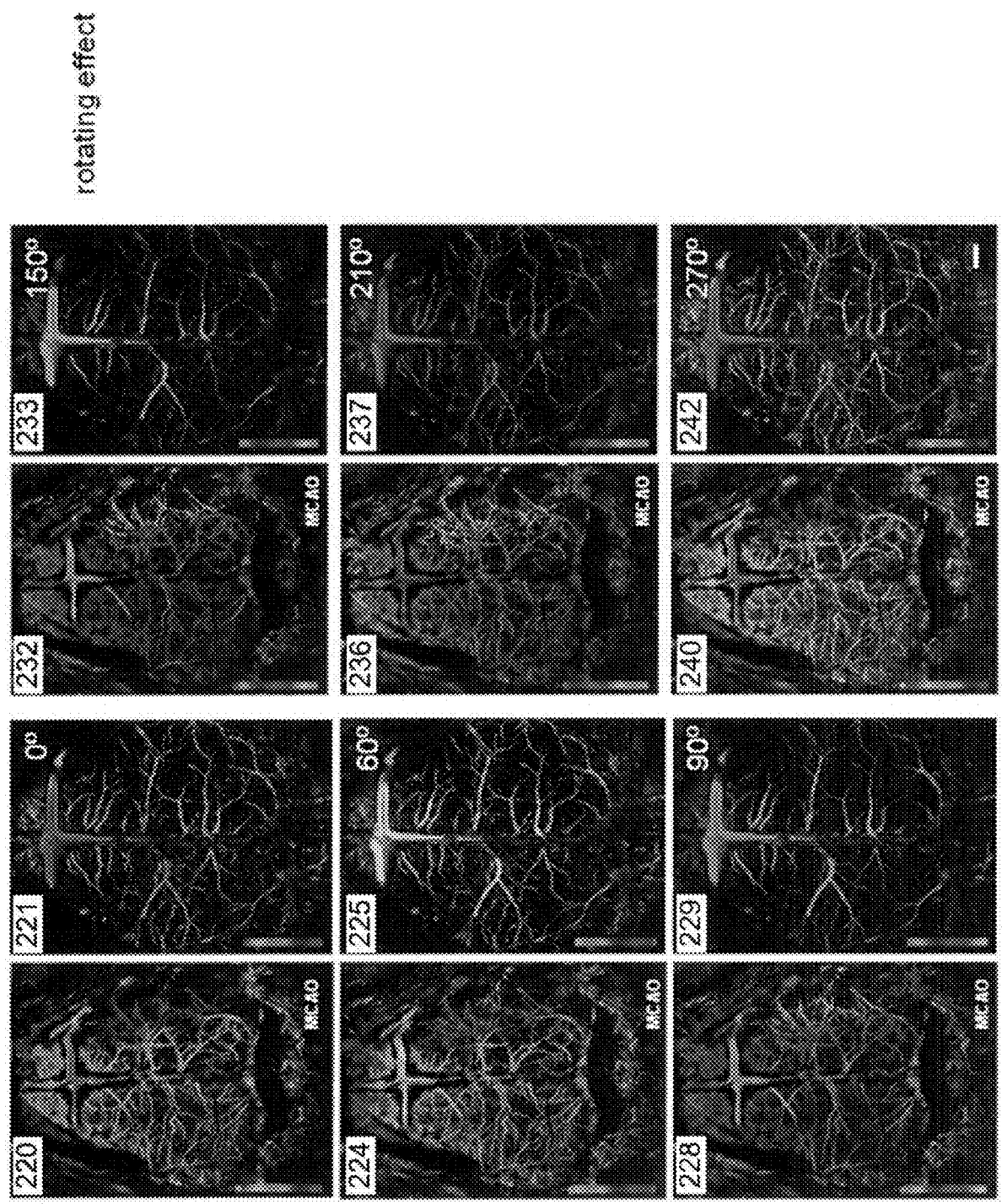

Reference is now additionally made to FIG. 2B, which is a simplified illustration of Hybrid DFLS images produced using transformations into a color space at various rotations of a color space axes according to an example embodiment of the invention.

The producing of the Hybrid DFLS image (c) 206 and image (f) 212 of FIG. 2A was performed by transformation of the LS image (a) 202 with the DF image (b) 204, and the LS image (d) 208 with the DF image (e) 210 respectively into the IHS color space.

However, combining the LS and DF images into the IHS color space may be performed at any rotation of the IHS color space.

FIG. 2B depicts images 220 224 228 232 236 240 of the brain of the MCA occluded mouse produced by transformation into different rotations of a IHS color space. The images 220 224 228 232 236 240 were transformed into the IHS color space with a Hue axis rotated at 0°, 30°, 60°, 90°, 150°, 210° and 270° respectively.

FIG. 2B depicts images 221 225 229 233 237 241 of the brain of the untreated control mouse produced by transformation into different rotations of a IHS color space. The images 221 225 229 233 237 241 were transformed into the IHS color space with a Hue axis rotated at 0°, 30°, 60°, 90°, 150°, 210° and 270° respectively.

It is noted that viewing the images at the various rotations may potentially emphasize or bring out a better view and potentially improve diagnostic efficacy.

In some embodiments of the invention, a user of the TOVI system may optionally input a color space rotation angle and produce a Hybrid DFLS image combined into a color space rotated by that angle.

In some embodiments of the invention, a user of the TOVI system may optionally rotate a knob, or slide a slider, whether a physical knob or slider or an implementation of the knob or slider on a touch screen, and cause a dynamic rotation of the color space, thereby potentially improving the display of the color image and potentially improving the efficacy of diagnosis.

In similar ways to those described above, TOVI can be used to examine hemodynamic changes during other pathologies and perturbation, such as disruption of blood-brain barrier (BBB), brain stimulation and other models of brain disorders.

An ability to observe in real time vascular response to treatment is potentially useful for drug development as well as for disease modeling.

An aspect of the present invention includes in vivo transcranial imaging of cortical blood vessels in mice which combines laser speckle imaging, fluorescent angiography and optionally displaying results via an IHS color model. TOVI enables a snapshotting of cortical hemodynamics, and provides potentially quickly panoramic views and dynamic color-mapped images of the functional cerebral vasculature, optionally without removing bone. These features potentially enable a rapid and accurate assessment of blood flow and perfusion in areas of the brain or in specific major or minor arteries and veins. The TOVI system is compact, and easily operated. The TOVI system includes several pieces of standard and affordable laboratory equipment. The minimally invasive technique associated with the TOVI system is a potentially powerful tool with which to monitor cortical hemodynamics in a variety of situations and for prolonged periods, making it potentially useful for various hemodynamic studies, and perhaps especially for quick-and-easy preclinical studies.

Reference is now additionally made to FIG. 3A, which is a set of four images depicting examples of LS images 302 304 306 308 produced according to an example embodiment of the invention.

FIG. 3A depicts examples of raw and enhanced laser speckle images.

Image (a) 302 depicts a raw LS image of an untreated control mouse.

Image (b) 304 depicts a LS image of a mouse with occlusion of the middle cerebral artery (MCAO).

Image (c) 306 depicts a LS image of an untreated control mouse.

Image (d) 308 depicts a LS image of a mouse with MCAO.

In the LS image 308 an area 309 is visible as suffering from occlusion, where blood vessels do not appear, and/or appear in less detail than a corresponding area in the other half of the brain. The corresponding raw image (b) 304 does not display enough details to show the occlusion.

In the example embodiment of FIG. 3A, images (c) 306 and (d) 308 are enhanced according to the formula described above $K=\sigma/<I>$.

In some embodiments, in the dynamic fluorescence (DF) mode, raw fluorescent images are acquired by the same camera, optionally during a 20 second time interval after fluorescent material administration, optionally at exposure time of 50 ms.

A Detailed Description of an Example Embodiment

Analysis of Fluorescence Intensity Dynamics

In the example experiment performed using an example embodiment of the invention, after contrast material administration, 400 raw images (exposure time: 45 ms per frame) were acquired. For each such experiment stacks of the first 200 (for example) raw DF image frames (optionally—10 seconds after the contrast agent first appeared in the cerebral vessels) were used for processing.

Image processing was optionally performed by using Fiji/ImageJ public domain software. First, spatial background subtraction was optionally performed in order to enhance visibility of CBVs. Spatial background subtraction is optionally based on an arithmetic difference between a raw image and a filtered raw image obtained using a spatial Gaussian filter, in which sigma was optionally empirically assigned to equal 10 pixels, as previously described. It is noted that the Gaussian filter may be assigned other sizes, such as in a range between 2 and 50 pixels, optionally depending on the sharpness, or resolution, of the image. Optionally, a 2D Frangi filter, which is also a standard Fiji plugin, was used to enhance linear structures for potentially better vessel visibility. Optionally, for each experiment, filtering is applied to each frame in the stack.

Function of Time

In the example embodiment, a distance that fluorescent material traveled inside the MCA was optionally measured using a straight line measurement tool (Line Selection) of the Fiji/ImageJ software. Distance was measured in arbitrary units (pixels) in order to avoid confusion.

In the example embodiment, following general anesthesia, the test animal was placed in a special holder with a warming plate, which assisted in maintaining a body temperature of ~37° C. and other vital signs. Next, the head of the test animal was gently shaved and residual fur was optionally removed by Veet hair removal cream (Reckitt Benckiser, Mannheim, Germany). After cream removal, the clear scalp was optionally subjected for 20 minutes (optionally in a range of 30 seconds to an hour) to a solution mixture (50/50) of glycerol and liquid paraffin oil. The solution is an optical clearing agent that is believed to improve transdermal imaging. Next, the mouse tail vein was catheterized and the mouse was placed under the microscope lens.

It is noted that in other example embodiments, other optical clearing agents are used to wet the scalp.

In the example embodiment, for DF imaging, a dose of 0.1 mg IR780 (Sigma Aldridge) in a volume of 50 microliters was injected into the tail vein.

A motivation for the above-described experimental embodiment study was to create an alternative to complicated and relatively expensive methods such as MRI, CT, PAT and OCT by developing a simple, non-invasive methodology for brain vessel imaging in vivo, with a potential focus on the MCA, and a potential for quantifying functional parameters related to the cerebral blood flow. The experimental approach described above is a non-invasive transcranial optical vascular imaging (also termed nTOVI). In addition to the use of NIR contrast materials the method described above takes advantage of relative transparency of an intact cranium and skin of young mice. It has been demonstrated that light propagation is sufficient for transcranial imaging in mice at the age of up to 6 months.

Figure 3B:
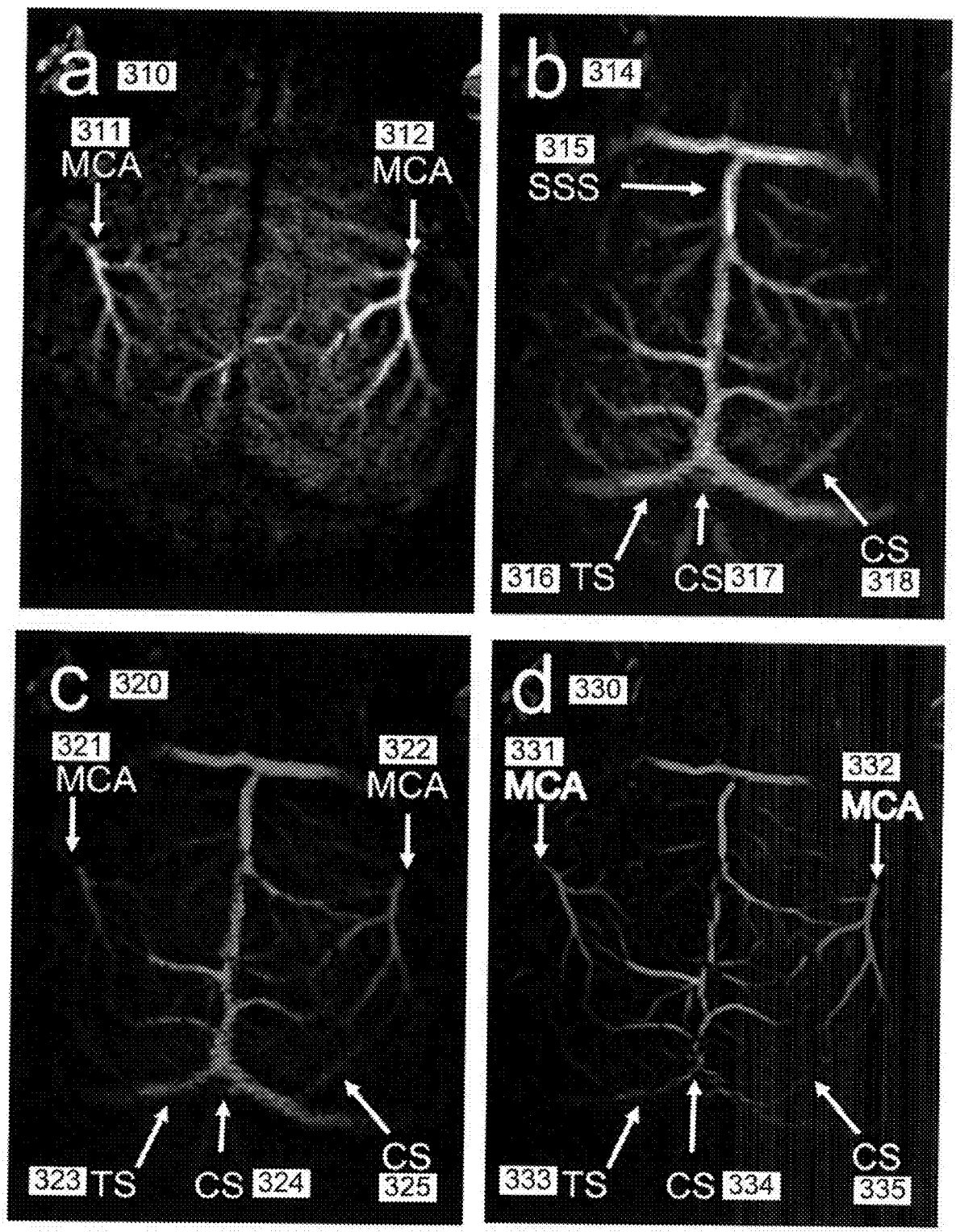

Reference is now additionally made to FIG. 3B, which is a set of four images depicting additional examples of images produced according to an example embodiment of the invention.

FIG. 3B depicts a first color-coded fluorescent intensity image 310 of an arterial phase ~1 second after contrast material arrival; arteries are clearly pronounced. MCA 311 312 (Middle Cerebral Artery); A second color-coded fluorescent intensity image 314 of a venous phase ~3 seconds after contrast material arrival; veins are clearly pronounced—e.g. 315 SSS (Superior Sagittal Sinus), Transverse Sinus 316, Cerebral Sinus 318 and Cerebral Sinus 318. A third color-coded superimposed image 320 of arterial (MCA 321 322) and venous phases showing arteries in red and veins in green—e.g. Transverse Sinus 323, Cerebral Sinus 324 and Cerebral Sinus 325; and a fourth color-coded vessel-enhanced superimposed image 330 of arterial (MCA 331 332) and venous phases—e.g. Transverse Sinus 333, Cerebral Sinus 334 and Cerebral Sinus 335.

FIG. 3B shows various modes of CBV visualization, which are based on enhancement of fluorescent raw images obtained through a skin surface, without damaging an integrity of the skull or the skin. Image enhancement was used in this example embodiment, improving image appearance and blood vessels demarcation.

In order to enhance perception and demarcation of different types of blood vessels a composite color-coded image was produced. In the composite image, data from an image of the arterial phase are coded as red, whereas the venous phase was coded as green. The color palette was chosen for convenience of perception. Left and right MCAs are clearly visible in an intensity color-coded image that corresponds with maximal visibility and distinguish-ability of arterial vessels (first color-coded fluorescent intensity image 310). In an intensity color coded image that corresponds with maximal visibility and distinguish-ability of the veins (second color-coded fluorescent intensity image 314), the venous sinuses are clearly visible. The third color-coded superimposed image 320 shows an RGB color-coded superimposed image of arterial and venous phases, in which arteries are seen in red and veins in green, whereas a similar image enhanced by Frangi filter, is shown in fourth color-coded vessel-enhanced superimposed image 330.

Figure 4A:
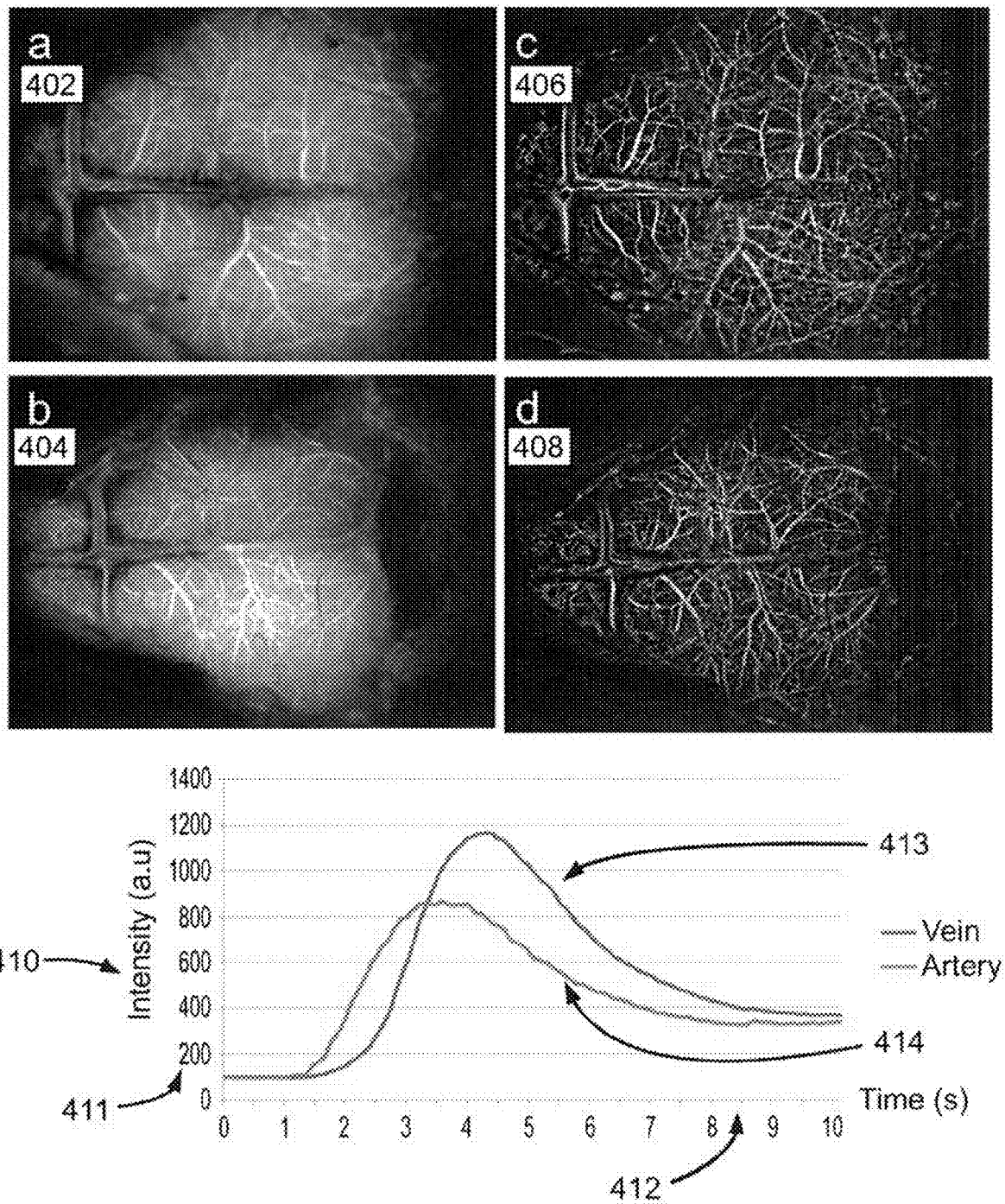

Reference is now additionally made to FIG. 4A, which depicts DF images 402 404 406 408 and a graph 410 produced according to an example embodiment of the invention.

Image (a) 402 depicts a Raw DF image of an untreated control mouse.

Image (b) 404 depicts a Raw DF image of a mouse with MCAO (Middle Cerebral Artery Occlusion).

Image (c) 406 depicts a Filtered Maximum Intensity Projection (FMIP) image of an untreated control mouse.

Image (d) 408 depicts a FMIP image of a mouse with MCAO.

Image (f) depicts a graph 410 showing fluorescence intensity 411 as a function of time 412 in representative vein 413 (green) and artery 414 (red) of an untreated mouse.

Examples of raw DF images are shown in FIG. 4A, images (a) 402 and (b) 404.

In some embodiments a video is obtained during the time interval after fluorescent material administration.

In some embodiments, no special mounting media is necessary.

Figure 4B:
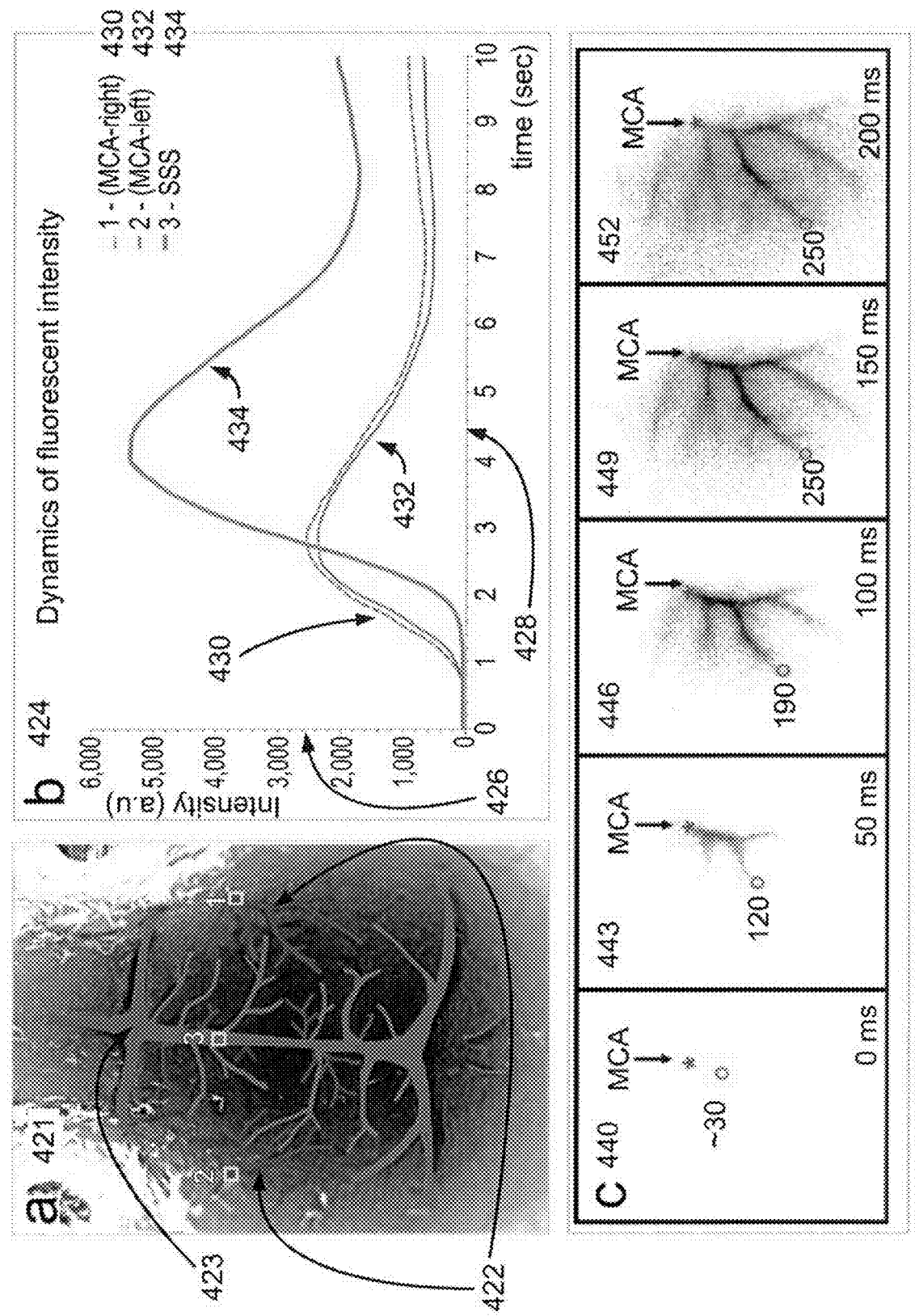

Reference is now made to FIG. 4B, which depicts DF images and a graph produced according to yet another example embodiment of the invention.

FIG. 4B depicts results of application of the nTOVI approach:

A first image 421 produced by a color mask superimposed on a monochrome bird's eye view image of a mouse head showing arterial (red) 422 and venous (green) 423 networks. The color mask is optionally produced artificially to mimic real blood vessels. Regions of interest (ROI), 10×10 pixels are marked: 1, right MCA; 2, left MCA; 3, superior sagittal sinus.

A graph 424 showing fluorescence intensity 426 as a function of time 428 in a representative vein 434 (green line), MCA-right artery 430 (dotted red line) and MCA-left artery 432 (solid red line).

Graph 424 shows changes in intensity of fluorescence over time after bolus injection of fluorescent material. A reasonably good difference is clearly seen between the region of interest (ROIs) marked by squares 3 and the ROIs marked by squares 1 and 2. The ROIs 1 and 2 show almost identical intensity, which may be interpreted as reflecting no MCA pathology, since the ROIs marked by 1 and 2 correspond to the MCA.

A set of additional images 440 443 446 449 452 depicts a sequence of individual frames of the MCA taken in 50 msec intervals. The images 440 443 446 449 452 show a progress of a fluorescent probe inside the vessel. The starting point is marked by an asterisk; circles mark final points of fluorescent probe visibility. Numbers indicate the distance traveled by the probe (as measured in pixels).

An ability to track the branches of a specific vascular tree such as of the MCA is potentially highly relevant to studies of stroke model in a specific artery, as well as to analysis of changes in a vascular tree over time, such as, by way of a non-limiting example, in carotid stenosis.

It is noted that NIR probes are typically less toxic than mid-NIR probes, which may also require more advanced, and hence potentially more expensive sensors and higher excitation energy. Thus, nTOVI is potentially a safe, simple and inexpensive method which nevertheless provides sufficient spatial resolution. Additionally, multiple administrations of contrast material are possible, potentially further increasing an ability to monitor hemodynamic changes over time and upon various interventions.

An artificial vascular mask image superimposed on the surface of the mouse scalp is shown in the first image 421. A color vascular mask was reconstructed using frame-by-frame analysis of a dynamic distribution of contrast material inside cerebral vessels. A quantitative analysis of contrast agent behavior may optionally be performed by measuring (plotting) fluorescent intensity as a function of time, as each ROI may correspond with a specific blood vessel. An example of such a graph plotted for three representative ROIs is presented in graph 424. As seen, the time point at which intensity starts to rise varies between arterial and venous vessels. No pronounced differences in dynamics between left and right MCAs was observed in the example experiment; such differences are potentially expected to be detected in case of MCA occlusion (a stroke).

To emphasize the benefits of nTOVI in relation to a time-series high-speed sampling in individual mice, a time-series of DF images is shown in the set of images 440 443 446 449 452, in which the MCA is visualized in intervals of 50 milliseconds (20 Hz). As a heart rate of mice might exceed 500 beats per minute, this approach potentially enables to detect even the effect of a single stroke volume. Moreover, high-speed imaging potentially allows tracing not only a pattern but also a speed of propagation of the fluorescent material, thus providing an indication of blood flow rate.

An example embodiment of an image processing flow is now described.

LS Image Rendering

Reference is again made to FIG. 1A.

Optionally, a stack of raw LS images 110 are streamed to a hard disk of an optional PC workstation 108, and optionally undergo computation 111, optionally producing resultant images 112.

As the top image of the stack of raw LS images 110 shows, a single LS image may be rather blurred. In the example embodiment depicted in FIG. 1A, for each experiment, 400 frames of unprocessed monochrome image illuminated by a diffused laser light were stacked. A specially developed macro for Fiji software, an open-source platform for biological image analysis based on ImageJ, was optionally used to compute perfusion images that can serve as a perfusion maps based on laser speckle contrast, as described above with reference to FIG. 3A. A non-limiting example of code for performing the calculation is presented in Appendix 1 below.

LS contrast images were optionally produced by statistical processing of 400 raw LS frames, optionally in groupings of 10 frames each, using the following equation:

$$K = \sigma/<I>$$

where K is laser speckle contrast, $\sigma$ is standard deviation of pixel intensity fluctuation over a given grouping, and $<I>$ is single pixel intensity for the same grouping. Typically, dark areas in the image correlate with higher blood perfusion, i.e. with blood vessels.

Examples of rendered LS images are also shown in FIG. 3A, images (c) 306 and (d) 308.

In the resultant images 112, functional blood vessels (larger than capillaries) are optionally imaged as dark areas. It is noted that the resultant images 112 are more detailed than the top image of the stack of raw LS images 110. Various blood vessels, functionality, and anatomical structures are optionally visualized by enhancing laser speckle image contrast as described above.

It is noted that in some embodiments, contrast of a laser speckle image is inversely proportional to a level of perfusion. In such embodiments, the contrast of an image with low perfusion is potentially high, and occluded blood vessels having low perfusion may be visualized.

In some embodiments hemodynamic data provided by the LS mode is used to identify an optimal time point for administration of a fluorescent probe material, potentially enhancing efficacy of DF imaging.

Figure 5A:
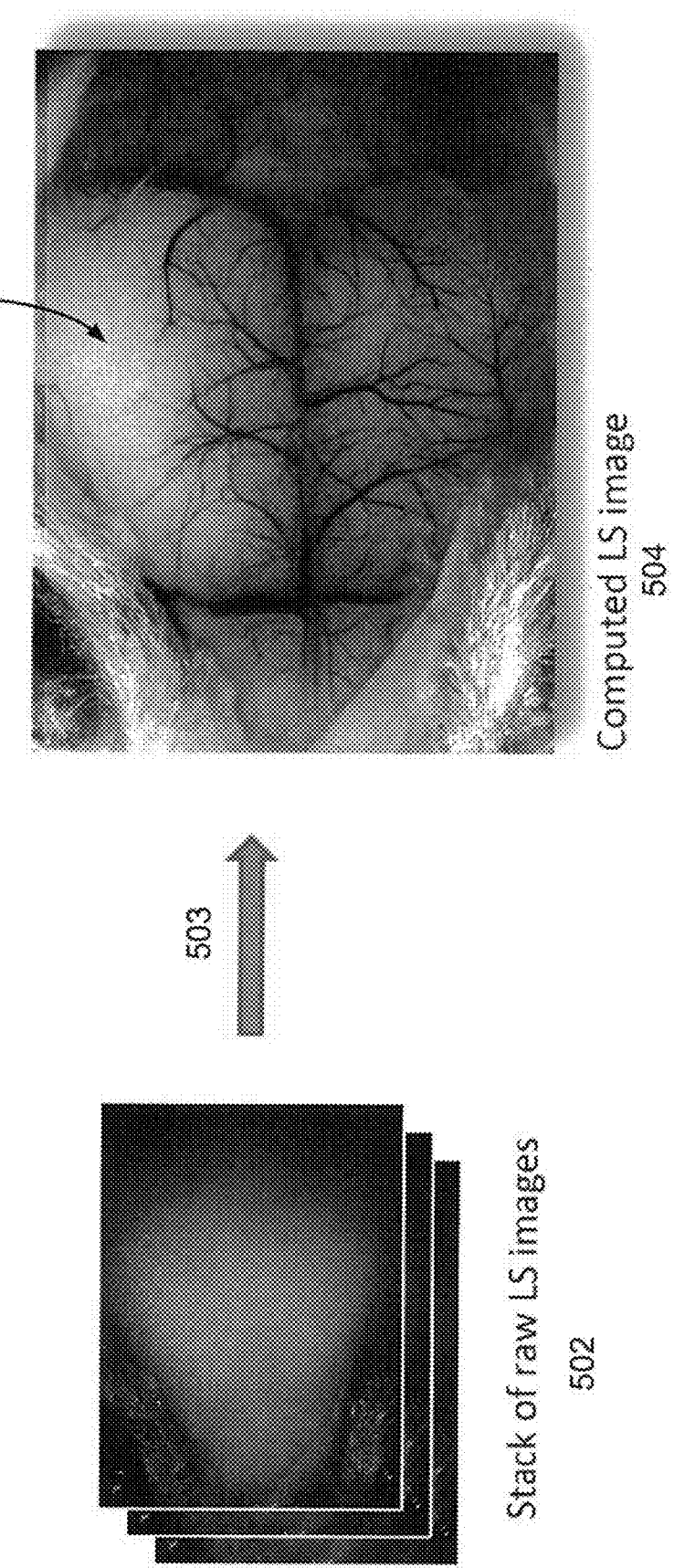

Reference is now additionally made to FIG. 5A, which is a simplified flowchart illustration of combining 503 a stack of raw LS images 502 into a resultant computed LS image 504 according to an example embodiment of the invention.

The top image of the stack of raw LS images 502 shows a single raw LS image which is rather blurred.

The computed LS image 504 displays a more detailed image than the single raw LS image from the stack of raw LS images 502, with a structure of blood vessels.

The computed LS image 504 also displays an area suffering from occlusion, where blood vessels do not appear, and/or appear in less detail than a corresponding area in the other half of the brain.

Reference is now additionally made to FIG. 5B, which is a simplified flowchart illustration of determining physiological information using LS images according to an example embodiment of the invention.

FIG. 5B depicts that a time sequence of raw LS images 510 can be used to produce a resultant computed LS image 514. FIG. 5B also depicts that additional information is also optionally determined. In the example embodiment depicted in FIG. 5B a graph 520 was produced, showing a change in laser speckle intensity over time. The graph 520 has an X-axis 522 showing time in units of seconds, and a Y-axis 521 showing laser speckle intensity in arbitrary, or relative, units. The graph 520 depicts a line 523 which demonstrates a change in speckle intensity, which corresponds to a change in an amount of blood which diffuses the laser speckles 1, and which corresponds to demonstrating a pulse rate of approximately 3 times per second, or a pulse rate of 180 per minute.

In some embodiments, the raw LS images are obtained at a rate higher than a pulse rate of the subject of the transcranial imaging. The obtained LS images optionally provide physiological information about the subject, such as the subject's pulse rate, potentially enabling decision about performing trials upon the subject. By way of a non-limiting example, a fluorescent material is optionally injected into the subject, in order to produce DF images, when the pulse rate of the subject demonstrates a specific physiological condition.

DF Imaging

In some example embodiments an intravenous fluorescein injection is administered to a subject, and multiple images of the subject are obtained by DF imaging. By way of a non-limiting example, 900 frames are acquired by DF, at an exposure time of 50 ms, and optionally streamed to the PC (reference 108 of FIG. 1A).

In the raw fluorescent image, for example one or more raw fluorescent images such as shown in reference 113 of FIG. 1A, blood vessels optionally appear as bright areas. Optionally, some acquired images, for example the first 400 frames, undergo filtering and fluorescence intensity is plotted as a function of time, for example as shown in the graph 410 of FIG. 4A. It is noted that the maximal fluorescence signal is detected in arteries approximately 1 second post injection, as compared to approximately 1.5 seconds post injection in veins, as displayed in a graph depicted as reference 114 of FIG. 1A and in the graph 410 of FIG. 4A. Various types of information on blood vessel kinetics are optionally extracted by measuring time and intensity in a DF image sequence. A non-limiting example of information which is optionally calculated by measuring time and intensity in a DF image sequence includes: differentiating between blood vessels such as arteries and veins; measuring perfusion in blood vessels; discriminating between functioning and less function and/or non-functioning blood vessels; blood vessels filling; blood vessel; and blood vessel leakage. Continuous DF data is optionally recorded frame by frame as a video, or movie, sequence. By watching the kinetics of blood flow, particular regions of interest are optionally determined.

DF Mode Image Processing

In some embodiments, for each experiment, stacks of raw DF image frames are analyzed. For example, in the images of FIG. 4A, 400 images were analyzed. Raw DF image are optionally enhanced using the Fiji software to improve visibility of blood vessel borders and to eliminate noise from the camera, as depicted in FIG. 4A, images (c) 406 and (d) 408.

An example embodiment of a flowchart of raw DF image enhancement and computation of filtered maximum intensity projection (FMIP) images from stacks of raw images is presented in FIG. 6.

Reference is now additionally made to FIG. 6, which is a simplified flowchart illustration of computing a filtered MIP (Maximum Intensity Projection) image from a stack of raw DF images according to an example embodiment of the invention.

FIG. 6 depicts a stack of raw DF images 602; a stack of blurred DF images 604, a stack of subtracted DF images 606, and a FMIP (Filtered Maximum Intensity Projection) image 608.

In some embodiments, a stack of blurred images 604 is optionally produced from an original stack of raw DF images 602, optionally using a Gaussian filter. For example reference 604 depicts blurred images produced using a Gaussian filter in Fiji with a setting of sigma=5 (pixels). In some embodiments the Gaussian filter approximately corresponds to a dimension (optionally width) of blood vessels in the images. In some embodiments the size of the Gaussian filter is optionally chosen to approximately correspond to a dimension of details which are desired, optionally blurring smaller background details. The resulting blurred stack 604 is then optionally subtracted from the raw stack 602, producing the stack of subtracted DF images 606.

Optionally, short-term fluctuations are smoothed out by calculating a moving average over the stack of subtracted DF images 606, producing the FMIP image 608.

In some embodiments, the smoothing is optionally using the following Fiji settings: 3D filter/Gaussian-Blur/X=0, Y=0, Z=3, where Z corresponds to an image order within the stack of subtracted DF images 606, or in other words Z corresponds to time.

In some embodiments a maximum intensity of each pixel is used to transform the stack of subtracted DF images 606 and produce the FMIP image 608.

DF image computation is optionally conducted, optionally followed by a computation of a HUE map.

It is noted that the MIP images may optionally be binary-valued, such as black and white, and still display blood vessel structure and information about perfusion, and movement of the fluorescent dye over time. In some embodiments, the MIP images are binary valued, and/or use a small number of bits for a grey scale. In some embodiments the MIP images use a standard number of bits for a grey scale, such as 8 or more bits.

Reference is now additionally made to FIG. 7, which is a simplified flowchart illustration of a generation of a HUE map from subtracted DF images according to an example embodiment of the invention.

FIG. 7 depicts a stack of subtracted DF images 702. The stack of subtracted DF images 702 optionally undergoes temporal blurring 704, producing a stack of temporal filtered (blurred) subtracted DF images 706.

The stack of temporal filtered (blurred) subtracted DF images 706 is optionally combined 708 to produce a HUE mapped image.

In some embodiments, for DF image computation, the IHS color model (intensity, hue, saturation) is used to produce a combined color image from source images of LS imaging and DF imaging. A normalized time is optionally calculated from a frame number having maximal pixel intensity (see graph 114 in FIG. 1A).

In some embodiments, time is encoded by a value of hue, which corresponds to color in IHS.

In some embodiments a Maximum Intensity Projection (MIP) is optionally calculated from raw fluorescent images, producing an anatomical pattern of blood vessels, and is optionally encoded by intensity and/or saturation.

In some embodiments specially developed Fiji macros were used, an example of which is presented below in Appendix 2.

In some embodiments a merging of combined color IHS images is optionally performed using the IHS Color Transforms plugin for Fiji software. In some embodiments, the plugin IHS_from_RGB is used to convert an RGB (Red, Green, Blue) image to the IHS (Intensity, Hue, Saturation) color space.

Hybrid (DFLS) Mode

Reference is now additionally made to FIG. 8, which is a simplified flowchart illustration of a generation of a color composite image based on an IHS color model according to an example embodiment of the invention.

FIG. 8 depicts a HUE mapped image 802 and a FMIP image 804. The HUE mapped image 802 and the FMIP image 804 are optionally combined 806, optionally producing a color composite image 808.

The flowchart of FIG. 8 depicts a computation of a color composite image 808 from FMIP and HUE mapped images.

In some embodiments, the FMIP image 804 is optionally mapped onto the Intensity and Saturation axes of the IHS color space, and the HUE mapped image 802 is optionally mapped onto the Hue axis.

In some embodiments, the FMIP image 804 is optionally mapped onto the Intensity axis of the IHS color space, and the HUE mapped image 802 is optionally mapped onto the Hue axis.

In some embodiments, the FMIP image 804 is optionally mapped onto the Saturation axis of the IHS color space, and the HUE mapped image 802 is optionally mapped onto the Hue axis.

In some embodiments, the FMIP image 804 is optionally mapped onto the colors red and blue, and the HUE mapped image 802 is optionally mapped onto the color green.

In the example embodiment depicted in FIG. 8, the FMIP image 804 was optionally mapped as Intensity in the IHS color model, the HUE map image 802 was optionally mapped as Hue in the IHS color model.

In some embodiments the color composite image 808 is optionally transformed into a RGB image. Optionally, the transformation to RGB may be done using the ImageJ IHS color Transforms plug-in of Martin Schluter (which is a standard RGB to IHS and IHS to RGB conversion method).

In some embodiments a computation produces a DF-image-based color-coded vascular map as described above with reference to FIG. 8. Optionally, in the IHS color map, hue represents a time point of maximum fluorescence, and intensity and/or saturation encode a maximum level of fluorescence. Thus, the color map demonstrates temporal information about blood flow. Because of the difference in arrival time of fluorescent material between arteries and veins, the main arteries appear in red-orange, major cortical veins appear in green and cranial veins in blue-purple, as depicted, by way of a non-limiting example, in the DF image of FIG. 1A, reference 116.

In some embodiments a hybrid mode is used, where images from the LS and DF imaging modalities are fused using the IHS color model. MIP images from DF mode are optionally encoded by intensity and saturation and the LS image is optionally encoded by hue.

In some embodiments, in a hybrid mode image, areas of high perfusion optionally appear as red whereas areas of low perfusion are seen as blue and purple.

Reference is now additionally made to FIG. 9, which is a simplified flowchart illustration of a generation of a color composite image based on an IHS color model according to another example embodiment of the invention.

FIG. 9 depicts a LS image 902 and a FMIP image 904. The LS image 902 and the FMIP image 904 are optionally combined 906, optionally producing a color composite image 908.

In some embodiments, the FMIP image 904 is optionally mapped onto the colors red and blue, and the LS image is optionally mapped onto the color green.

In some embodiments, the FMIP image 904 is optionally mapped as Intensity in the IHS color model, and the LS image 902 is optionally mapped as Hue in the IHS color model.

In some embodiments, the FMIP image 904 is optionally mapped as Saturation in the IHS color model, and the LS image 902 is optionally mapped as Hue in the IHS color model.

In the example embodiment depicted in FIG. 9, the FMIP image 904 was optionally mapped as Intensity and Saturation in the IHS color model, and the LS image 902 was optionally mapped as Hue in the IHS color model.

In some embodiments the color composite image 908 is optionally transformed into a RGB image. Optionally, the transformation to RGB may be done using the ImageJ IHS color Transforms plug-in of Martin Schluter (which is a standard RGB to IHS and IHS to RGB conversion method).

In some embodiments, in a hybrid DFLS mode, the IHS color model is optionally used to produce a color mapping of perfusion based on data acquired by both modalities. The maximum fluorescence level calculated from DF images is optionally encoded as intensity and saturation, whereas the contrast extracted from LS images is encoded as hue. This means that areas with high perfusion are seen in red, as depicted, by way of a non-limiting example, in the Hybrid DFLS image of FIG. 1A, reference 118 and in the flowchart of FIG. 9.

Subject Preparation and Fluorescein Administration

In some embodiments, following administration of general anesthetics to a subject, an initial cut is optionally made and the skin over the frontal, temporal, occipital and parietal regions is optionally removed by blunt dissection.

In some embodiments, an exposed area is optionally moistened with saline.

In some embodiments, a subject, by way of a non-limiting example a mouse, is placed under a microscope (e.g. reference 101 of FIG. 1A) lens, on a subject (mouse) holder with a warming plate (e.g. reference 106 of FIG. 1A), which optionally maintains a constant body temperature.

In some embodiments, for fluorescence imaging, a dose of 0.025 mg fluorescein in a volume of 100 microliters is optionally injected into a mouse tail vein.

Middle Cerebral Artery Occlusion (MCAO)

An example embodiment of a trial imaging is now described, performing an imaging of a middle cerebral artery occlusion (MCAO).

MCAO was performed generally as described above, with the following modifications. Anesthesia was performed by intra-peritoneal injection of ketamine (10 mg\kg) and xylazine (100 mg\kg) mixture, as described in the above-mentioned article titled: "In vivo characterization of tumor and tumor vascular network using multi-modal imaging approach" by Kalchenko, et al. A monofilament MCAO suture by Doccol Corporation, Sharon, Mass., USA, with a diameter of 0.20 mm was used.

A Short Discussion of Potential Advantages

Example embodiments of the present invention potentially teach a noninvasive, robust and safe approach for high-speed optical imaging of cerebral blood vessels in experimental subject. The approach described herein potentially enables imaging of major cerebral blood vessels, optionally without violating an integrity of a skull and of a skin of the scalp. The methodology optionally uses an analysis of the fast dynamics of fluorescence produced by a contrast agent after its introduction into blood circulation. Optionally combining DF analysis with digital processing of a sequence of images, by way of a non-limiting example by using freely available software such as ImageJ, and optionally with color coding, potentially enables to distinguish between arteries and veins and to identify the boundaries of vessels, such as MCA and main veins. Analysis of the dynamics of fluorescent intensity in a specific vessel potentially enables measurement of a velocity of blood flow.

In some embodiments the above-described methods are considered especially for use on mice and similar small animals of up to six months of age, therefore, are highly useful for preclinical trials, especially in the development of new CNS drugs, and for analysis of cerebral circulation disorder models.

In some embodiments the above-described methods are suitable for use after craniotomy in any operation in order to visualize the vascular tree and blood flow. In such cases the methods may be used on humans after craniotomy, or other mammals, vertebrates, or any animal in which blood flow is to be mapped.

In some embodiments the above-described methods are suitable for use for visualizing brain emboly and massive brain emboly in any situation, particularly after craniotomy. Again, in such cases the methods may be used on humans, or other mammals, vertebrates, or any animal in which blood flow is to be mapped.

In some embodiments the above-described methods are suitable for use to monitor brain development through an open fontanel in the first months of life of a human baby. In such cases the methods may be used on human babies, or other animals which are born with an open fontanel.

In some embodiments an optic fiber is optionally implanted together with electrodes which are implanted in a brain in DBS (deep brain stimulation) potentially in order to implement TOVI. The optic fiber may optionally serve for excitation and optionally for delivery of signals to the microscope. Such embodiments potentially enable monitoring vascular tree changes in parallel to DBS, and potentially enable examining effects of DBS. In an example embodiment, blood vessels are optionally imaged by TOVI in order to monitor for potentially harmful effects of DBS which might cause BBB (blood brain barrier) defects and potentially cause brain damage.

It is expected that during the life of a patent maturing from this application many relevant laser speckle imaging techniques will be developed and the scope of the term laser speckle imaging is intended to include all such new technologies a priori.

It is expected that during the life of a patent maturing from this application many relevant dynamic fluorescent imaging techniques will be developed and the scope of the term dynamic fluorescent imaging is intended to include all such new technologies a priori.

As used herein the terms "about" and approximately refer to ±25%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

An Example Method of Transcranial Brain Optical Imaging

Reference is now additionally made to FIG. 10, which is a simplified flowchart illustration of a method of transcranial brain optical imaging according to an example embodiment of the invention which includes:

obtaining a Laser Speckle (LS) image of cranial blood vessels of a subject through a non-thinned cranium (1005);

obtaining a Dynamic Fluorescence (DF) image of the cranial blood vessels of the subject through the non-thinned cranium (1010);

combining the LS image and the DF image producing a combined color image which displays both structure of the cranial blood vessels and perfusion of fluorescent material along the cranial blood vessels (1015).

A Second Example Method of Transcranial Brain Optical Imaging

Reference is now additionally made to FIG. 11, which is a simplified flowchart illustration of a method for producing a medical image which displays change of a medical subject over time according to an example embodiment of the invention and which includes:

obtaining a first medical image of the medical subject (1105);

obtaining a second medical image of the medical subject (1110); and producing a combined color image based on the first medical image and the second medical image (1115) wherein, for each pixel in the first medical image:

setting an Intensity value of the pixel in the combined color image based, at least in part, on a value of a corresponding pixel in the first medical image (1120); and setting a Hue value of the pixel in the combined color image based, at least in part, on a difference between the value of the corresponding pixel in the first medical image and the value of the corresponding pixel in the second medical image (1125).

A Third Example Method of Transcranial Brain Optical Imaging

Reference is now additionally made to FIG. 12, which is a simplified flowchart illustration of a method for producing a medical image by hybrid DFLS imaging according to an example embodiment of the invention.

The method of FIG. 12 includes:

producing a stack of raw LS images (1202);

producing an LS image of blood vessels (1204);

calculating a velocity distribution of blood in blood vessels (1206), optionally by measuring a velocity of advance of fluorescent material through the blood vessels;

producing a stack of DF images (1208);

producing a DF image of blood arteries (1210);

based on the DF images, calculating a velocity distribution of blood in arteries (1212), optionally by measuring a velocity of advance of fluorescent material through the arteries;

producing a DF image of blood veins (1214);

based on the DF images, calculating a velocity distribution of blood in veins (1216), optionally by measuring a velocity of advance of fluorescent material through the veins;

producing a fused, or combined, color coded image of arteries and veins, including blood flow velocity indications (1218).

As described above in the section titled "A short overview", in some embodiments, when arteries and veins have been distinguished, an analysis of velocity, flow rate etc, is optionally performed separately for arteries and for veins, and the analysis is optionally improved by knowing reasonable ranges for values of the measured parameters.

APPENDIX 1

An example macro for Fiji for computation of LS image from raw LS image stack

```
//***************************************************
// LS Plugin v1.04 Feb 2014
// Laser Speckle Imaging
```

APPENDIX 1-continued

An example macro for Fiji for computation of LS image from raw LS image stack

```
// IntegraCon = 10 frames
// Vyacheslav (Slava) Kalchenko, MD, PhD, FRMS
// In Vivo OpCcal Imaging Unit
// Department of Veterinary Resources
// Weizmann Institute of Science
// email: a.kalchenko@weizmann.ac.il
//***************************************************
name = getTitle;
Raw=getImageID( );
setBatchMode(true);
run("Grouped Z Project...", "projecCon=[Standard DeviaCon] group=10");
Sd=getImageID( );
selectImage(Raw);
run("Grouped Z Project...", "projecCon=[Average Intensity] group=10");
Mean=getImageID( );
selectImage(Raw);
close( );
imageCalculator("Divide create 32--□bit stack", Sd, Mean);//
Rstack=getImageID( );
selectImage(Rstack);
run("Z Project...", "start=1 stop=1000 projecCon=[Average Intensity]");
Result1=getImageID( );
selectImage(Rstack);
close( );
selectImage(Mean);
close( );
selectImage(Sd);
close( );
selectImage(Result1);
rename ("LSI" + "_" + name);
setBatchMode(false);
```

APPENDIX 2

An example macro for Fiji for computation of HUE map image from enhanced subtracted DF image stack

```
//TCM Time Color Mapping - FAST 11.11.13
//Currently this program produces HUE map for IHS or HSV color space
//hue = (index of the image of the maximum value for the pixel)/(images per hue cycle)
//Author:
//Vyacheslav (Slava) Kalchenko, MD, PhD, FRMS
//In Vivo OpCcal Imaging Unit
//Department of Veterinary Resources
//Weizmann Institute of Science
//email: a.kalchenko@weizmann.ac.il
setBatchMode(true);
path = File.openDialog("Select a File");
open(path);
scr=getImageID( );
Stack.getStaCsCcs(voxelCount, mean, min, max, stdDev);
run("32-bit");
run("Divide...", "value="+max):
y=getHeight( );
x=getWidth( );
newImage("hue", "32-bit black", x, y, 1);
hue=getImageID( ); //New image for Hue
progress=0;
step=1/(x*y);
for(j=0;j<y;j++) {
    for (i=0;i<x;i++) {
        progress=progress+step;
        showProgress(progress);
//_____ find HUE value <h>_____
map=0;
h=0; //first Hue parameter
selectImage(scr);
```

APPENDIX 2-continued

An example macro for Fiji for computation of HUE map image from enhanced subtracted DF image stack

```
for(s=1;s<nSlices;s++) {
    setSlice(s);
    ps=getPixel(i,j); //    current pixel
    if (map==ps){h=s;} // index of maximal value <<h>>
        if (map<ps){map=ps;}// find maximum
}
//_____ end find HUE value <h>_____
hn=(h/nSlices); //--< hn >---- normalisaCon on number of frames
selectImage(hue);
setPixel(i,j,hn);
        }
}
setBatchMode(false);
//*********************************************
```

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of transcranial brain optical imaging comprising:
    obtaining a Laser Speckle (LS) image of cranial blood vessels of a subject;
    obtaining a Dynamic Fluorescence (DF) image of the cranial blood vessels of the subject; and
    combining the LS image and the DF image producing a combined color image which displays both structure of the cranial blood vessels and perfusion of blood along the cranial blood vessels,
    and further comprising using a filtering component in the optical path of the optical system configured to exchange between an optical filter for passing light in a wavelength of a laser used for obtaining the LS image and an optical filter used for passing light in a wavelength of fluorescent light used for obtaining the DF image,
    wherein the obtaining the LS image, obtaining the DF image and combining the LS image and the DF image produces the combined color image of intracranial blood vessels through an intact cranium; and
    the optical filter for passing light in a wavelength of fluorescent light used for obtaining the DF image is in a range between 660 and 900 nm.

2. The method of claim 1 in which the structure of the cranial blood vessels is displayed as Intensity in the combined color image and the perfusion is displayed as Hue in the combined color image.

3. The method of claim 1 in which the perfusion of blood is displayed based, at least in part, on the DF image.

4. The method of claim 1 in which the structure of the cranial blood vessels is displayed based, at least in part, on the DF image.

5. The method of claim 1 in which a plurality of different DF images are obtained at different times and are displayed as different colors in the combined color image.

6. The method of claim 1 where the combined color image is produced by combining values from the LS image and the DF image into a value in an Intensity, Hue, Saturation (IHS) color space.

7. The method of claim 6 in which the structure of the cranial blood vessels is displayed as Intensity and the perfusion of fluorescent material along the cranial blood vessels is displayed as Hue.

8. The method of claim 6 in which a value of a pixel in the combined color image corresponds to a transformation of a value of a corresponding pixel in the LS image and a corresponding pixel in the DF image into a rotated IHS color space.

9. The method of claim 1 where the combined color image is produced by combining values from the LS image and the DF image into a value in the IHS color space, and in which, for each pixel in the combined color image:
    setting an Hue value of the pixel in the combined image based, at least in part, on a value of a corresponding pixel in the LS image; and
    setting an Intensity value of the pixel in the combined color image based, at least in part, on a time of obtaining the DF image along a time axis.

10. The method of claim 1 in which the subject of the transcranial brain optical imaging is thinned to a cranium thickness of between 0.25 millimeters and 1 millimeter.

11. The method of claim 1 in which the LS image and the DF image are captured through a non-thinned cranium.

12. The method of claim 1 in which the LS image and the DF image are captured through an intact skin.

13. The method of claim 1 in which the LS image and the DF image are captured through an open fontanel of a baby in the first months of life.

14. The method of claim 1 wherein the subject of the transcranial brain optical imaging is a subject having a cranium thickness in a range between 0.25 millimeters and 1 millimeter.

15. The method of claim 1 and further comprising using Near Infra Red fluorescent probe materials, emitting radiation in a range between 700 to 1300 nm wave lengths, to obtain the Dynamic Fluorescence (DF) image.

16. The method of claim 1 wherein the using the filtering component comprises exchanging between the optical filter for passing light in the wavelength of the laser used for obtaining the LS image and the optical filter used for passing light in the wavelength of fluorescent light used for obtaining the DF image.

17. A method of transcranial brain optical imaging comprising:
    obtaining a Laser Speckle (LS) image of cranial blood vessels of a subject;
    obtaining a Dynamic Fluorescence (DF) image of the cranial blood vessels of the subject; and
    combining the LS image and the DF image producing a combined color image which displays both structure of the cranial blood vessels and perfusion of blood along the cranial blood vessels,
    and further comprising using a filtering component in the optical path of the optical system configured to exchange between an optical filter for passing light in a wavelength of a laser used for obtaining the LS image and an optical filter used for passing light in a wavelength of fluorescent light used for obtaining the DF image, wherein:

the obtaining the LS image, obtaining the DF image and combining the LS image and the DF image produces the combined color image of intracranial blood vessels through an intact cranium and further comprising:

obtaining a plurality of the LS images of the cranial blood vessels of the subject at different times; and calculating a heart rate of the subject of the transcranial brain optical imaging based, at least in part, on a rate of a varying of intensity of the plurality of the LS images.

18. A method of transcranial brain optical imaging comprising:

obtaining a Laser Speckle (LS) image of cranial blood vessels of a subject;

obtaining a Dynamic Fluorescence (DF) image of the cranial blood vessels of the subject; and combining the LS image and the DF image producing a combined color image which displays both structure of the cranial blood vessels and perfusion of blood along the cranial blood vessels, and further comprising using a filtering component in the optical path of the optical system configured to exchange between an optical filter for passing light in a wavelength of a laser used for obtaining the LS image and an optical filter used for passing light in a wavelength of fluorescent light used for obtaining the DF image, wherein the obtaining the LS image, obtaining the DF image and combining the LS image and the DF image produces the combined color image of intracranial blood vessels through an intact cranium;

a plurality of DF images are obtained at different times; and further comprising calculating a blood flow rate based, at least in part, on differences between the plurality of DF images.

19. A method of transcranial brain optical imaging comprising:

obtaining a Laser Speckle (LS) image of cranial blood vessels of a subject;

obtaining a Dynamic Fluorescence (DF) image of the cranial blood vessels of the subject; and combining the LS image and the DF image producing a combined color image which displays both structure of the cranial blood vessels and perfusion of blood along the cranial blood vessels, and further comprising using a filtering component in the optical path of the optical system configured to exchange between an optical filter for passing light in a wavelength of a laser used for obtaining the LS image and an optical filter used for passing light in a wavelength of fluorescent light used for obtaining the DF image, wherein the obtaining the LS image, obtaining the DF image and combining the LS image and the DF image produces the combined color image of intracranial blood vessels through an intact cranium, and further comprising:

obtaining a plurality of the LS images of the cranial blood vessels of the subject at different times;

calculating a heart rate of the subject of the transcranial brain optical imaging based, at least in part, on a rate of a varying of intensity of the plurality of the LS images;

obtaining a plurality of the DF images of the cranial blood vessels of the subject at different times;

calculating a blood flow rate based, at least in part, on differences between the plurality of the DF images; and comparing the heart rate to the blood flow rate.

20. Apparatus for transcranial brain optical imaging comprising:

a laser for laser illumination of a subject of transcranial brain optical imaging;

a lamp for exciting fluorescence in the subject of transcranial brain optical imaging; and an optic system for collecting light from the subject of the transcranial brain optical imaging to a camera for capturing transcranial brain optical images; and a camera for capturing transcranial brain optical images from the optic system, wherein the optic system comprises a common optical path for both laser light scattered from the subject and fluorescent light emitted from a fluorescent dye excited by the lamp for exciting fluorescence, and further comprising a filtering component in the optical path of the optical system configured to exchange between an optical filter for passing light in a wavelength of the laser and an optical filter for passing light in a wavelength of the fluorescent light, wherein the optical filter for passing light in a wavelength of fluorescent light is in a range between 660 and 900 nm.

21. A method of transcranial brain optical imaging comprising:

obtaining a Laser Speckle (LS) image of cranial blood vessels of a subject;

obtaining a Dynamic Fluorescence (DF) image of the cranial blood vessels of the subject; and combining the LS image and the DF image producing a combined color image which displays both structure of the cranial blood vessels and perfusion of blood along the cranial blood vessels, and further comprising using a filtering component in the optical path of the optical system configured to exchange between an optical filter for passing light in a wavelength of a laser used for obtaining the LS image and an optical filter used for passing light in a wavelength of fluorescent light used for obtaining the DF image, wherein the obtaining the LS image, obtaining the DF image and combining the LS image and the DF image produces the combined color image of intracranial blood vessels through an intact cranium;

the obtaining the LS image comprises:

obtaining a plurality of LS images; and using the plurality of LS images to calculate an improved-contrast LS image; and the combining comprises combining the improved-contrast_LS image and the DF image, thereby producing the combined color image.

* * * * *